US012586096B2

(12) United States Patent
Ozminkowski et al.

(10) Patent No.: US 12,586,096 B2
(45) Date of Patent: Mar. 24, 2026

(54) MODELING AND BENCHMARKING HEALTH CARE AFFORDABILITY AND AVAILABILITY

(71) Applicant: Aon Global Operations SE, Singapore Branch, Singapore (SG)

(72) Inventors: Ronald J. Ozminkowski, Saline, MI (US); Yifei Dai, Chicago, IL (US); Geoffrey Kuhn, Singapore (SG); Xiang Ying Ho, Singapore (SG); Jonathan Bowen, Denver, CO (US); Todor Penev, Atlanta, GA (US); Weiyee Lee, Singapore (SG); Leanne Metcalfe, Cedar Creek, TX (US); Andrew C. Rallis, Singapore (SG); Eric Peng, Irvine, CA (US)

(73) Assignee: Aon Global Operations SE, Singapore Branch, Singapore (SG)

( * ) Notice: Subject to any disclaimer, the term of this patent is extended or adjusted under 35 U.S.C. 154(b) by 0 days.

(21) Appl. No.: 18/884,290

(22) Filed: Sep. 13, 2024

(65) Prior Publication Data

US 2025/0095015 A1     Mar. 20, 2025

Related U.S. Application Data

(60) Provisional application No. 63/538,450, filed on Sep. 14, 2023.

(51) Int. Cl.
*G06Q 30/0201* (2023.01)
*G06Q 10/1057* (2023.01)
(Continued)

(52) U.S. Cl.
CPC ..... *G06Q 30/0206* (2013.01); *G06Q 10/1057* (2013.01); *G06Q 30/0283* (2013.01);
(Continued)

(58) Field of Classification Search
CPC ........... G06Q 30/0206; G06Q 10/1057; G06Q 30/0283; G06Q 40/08; G16H 50/30; G16H 50/70
See application file for complete search history.

(56) References Cited

U.S. PATENT DOCUMENTS

| | | | |
|---|---|---|---|
| 11,347,829 B1 | 5/2022 | Sclar et al. | |
| 2016/0253687 A1* | 9/2016 | Wei | G06F 16/86 705/3 |

(Continued)

OTHER PUBLICATIONS

Greer ML, Zayas CE, Bhattacharyya S. Repeatable enhancement of healthcare data with social determinants of health. Front Big Data. Aug. 1, 2022;5:894598. doi: 10.3389/fdata.2022.894598. PMID: 35979428; PMCID: PMC9376253. (Year: 2022).*

(Continued)

*Primary Examiner* — George Chen
*Assistant Examiner* — Tayar M Kyu
(74) *Attorney, Agent, or Firm* — Finch & Maloney PLLC

(57) ABSTRACT

In an illustrative embodiment, methods and systems for modeling health care affordability across a population includes segmenting the population by demography and/or geography, determining chronic condition distribution across the population segments, modeling, across the population segments, medical service utilization distribution for a set of medical services, and calculating, using unit costs for each of the set of medical services, utilization costs for each population segment. The methods and systems may include calculating relative affordability metrics based on the utilization costs.

19 Claims, 16 Drawing Sheets

(51) Int. Cl.
*G06Q 30/0283* (2023.01)
*G06Q 40/08* (2012.01)
*G16H 50/30* (2018.01)
*G16H 50/70* (2018.01)

(52) U.S. Cl.
CPC ............. *G06Q 40/08* (2013.01); *G16H 50/30* (2018.01); *G16H 50/70* (2018.01)

(56) References Cited

U.S. PATENT DOCUMENTS

| | | | |
|---|---|---|---|
| 2017/0212997 | A1 | 7/2017 | Buonfiglio et al. |
| 2021/0110351 | A1* | 4/2021 | Wang ..................... G16H 10/20 |
| 2021/0174968 | A1 | 6/2021 | Butterfield et al. |
| 2021/0383932 | A1 | 12/2021 | Kobetz et al. |
| 2022/0319717 | A1* | 10/2022 | Henderson, Jr. ....... G16H 50/20 |
| 2024/0126822 | A1* | 4/2024 | Hamilton ............ G06F 16/9538 |
| 2024/0186012 | A1* | 6/2024 | Gupta ................... G16H 50/80 |

OTHER PUBLICATIONS

McKinsey Health Institute, "Vulnerable Populations: Data by Geography", 2021.

\* cited by examiner

200

About Your Employees _404_

Affordability _418_
23.6% of employees spend over 10% of their income on healthcare, compared to 23.2% Agriculture, Forestry, Fishing industry benchmark

Area Deprivation Index (ADI) _420_
Of those who struggle with affordability (spend>10%), 38.1% of employees live in high ADI risk areas

Primary Care Physician Shortage _422_
Of those who struggle with affordability (spend>10%), 32.3% of employees live in areas with high PCP shortage

Mental Health Provider Shortage _424_
Of those who struggle with affordability (spend>10%), 70.1% of employees live in areas with high MH provider shortage

About Your Company _402_

Industry: Agriculture, Forestry, Fishing   _406_

Employees Enrolled: 40,592   _408_

Gender: 44% Female / 56% Male   _410_

Average Age: 44   _412_

Average Salary[1]: $91,242 (estimated) _414_

| Salary Band[1] | Employee Count | % of Employees |
|---|---|---|
| $0-$30k | 1,665 | 4% |
| $30-$50k | 11,351 | 28% |
| $50-$70k | 7,183 | 18% |
| $70-$100k | 6,169 | 15% |
| Above $100k | 14,224 | 35% |

Alcohol Consumption/1k     _702a_

Obesity/1k     _702b_

Tobacco Consumption/1k     _702c_

Poor Nutrition/1k     _702d_

ADI Risk:  Low  _704a_   Medium  _704b_   High  _704c_

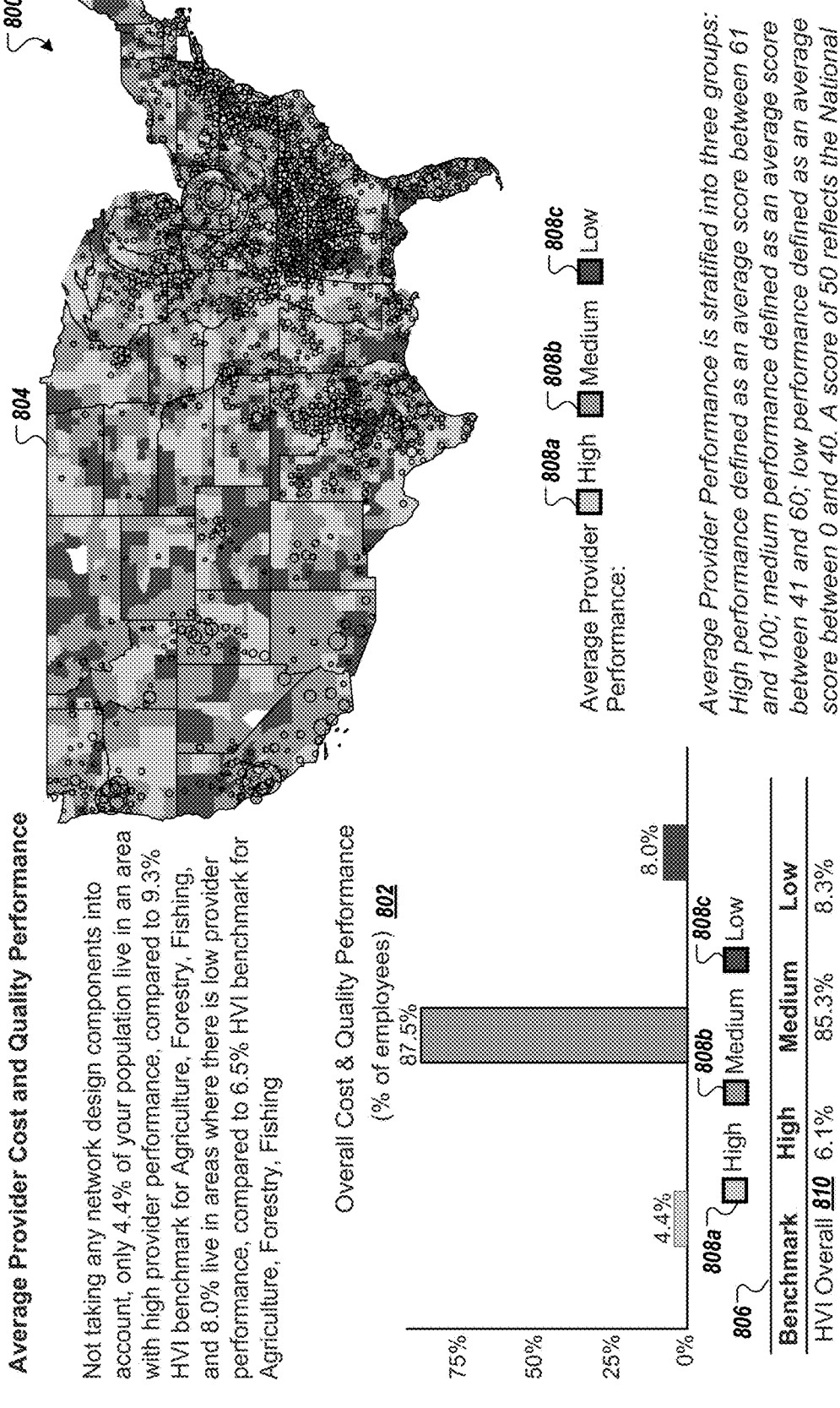

Average Provider Cost and Quality Performance

Not taking any network design components into account, only 4.4% of your population live in an area with high provider performance, compared to 9.3% HVI benchmark for Agriculture, Forestry, Fishing, and 8.0% live in areas where there is low provider performance, compared to 6.5% HVI benchmark for Agriculture, Forestry, Fishing Overall Cost & Quality Performance (% of employees) *802*

808a — High    808b — Medium    808c — Low

806

| Benchmark | High | Medium | Low |
|---|---|---|---|
| HVI Overall *810* | 6.1% | 85.3% | 8.3% |
| HVI Industry *812* | 9.3% | 83.9% | 6.5% |

Average Provider Performance:

808a — High    808b — Medium    808c — Low

*Average Provider Performance is stratified into three groups: High performance defined as an average score between 61 and 100; medium performance defined as an average score between 41 and 60; low performance defined as an average score between 0 and 40. A score of 50 reflects the National Average.*

FIG. 8A

MODELING AND BENCHMARKING HEALTH CARE AFFORDABILITY AND AVAILABILITY

RELATED APPLICATIONS

This application claims the benefit of and priority to U.S. Provisional Patent Application Ser. No. 63/538,450 entitled "Modeling and Benchmarking Health Care Affordability and Availability" and filed Sep. 14, 2023. This application is related to the following prior patent applications: U.S. patent application Ser. No. 16/880,539 entitled "Optimizing Benefits Selection in View of Both Member Population and Organized Preferences" filed May 21, 2020 (now U.S. Pat. No. 11,636,435), U.S. patent application Ser. No. 16/554, 157 entitled "Optimizing Benefits Selection in View of Both Member Population and Organized Preferences" filed Aug. 28, 2019 (now U.S. Pat. No. 10,664,806), and U.S. patent application Ser. No. 15/900,705 entitled "Dashboard Interface, Platform, and Environment for Intelligent Subscription Product Selection" filed Feb. 20, 2018 (now U.S. Pat. No. 10,402,788). All above identified applications are hereby incorporated by reference in their entireties.

BACKGROUND

Employers and subscribers face many challenges to achieve positive health outcomes including affordability and equal access to care. Factors such as varying debt burdens, wages, premium contributions, and cost of care result in an affordability gap where insured individuals lack the disposable income to afford the annual cost of anticipated, typical medical expenses such as copays, deductibles, and other out-of-pocket costs for themselves and/or their family members. Individuals experiencing healthcare access difficulties due to cost are considered "functionally underinsured." When individuals are faced with lack of adequate funds for healthcare, they often make decisions that are detrimental to their well-being such as avoiding or delaying preventative care, skipping medication, or taking less than prescribed doses of medications to stretch the allocated prescription. Further, the budgetary burden on the functionally underinsured often results in higher stress, lower work productivity, fewer preventative care visits, a diminished relationship with their primary care provider, and a higher amount of household debt.

Health outcomes are further impacted by uneven geographical distribution of health providers by population density. A Health Professional Shortage Area (HPSA) is a geographic area, population group, or health care facility that has been designated by the Health Resources and Services Administration (HRSA) as having a shortage of health professionals. In September of 2022, the Kaiser Family Foundation noted that 97.6 million people in the U.S. live in a designated HPSA, and more than 16,900 additional practitioners would be needed to remove the HPSA designation. In addition to primary care, maternal care, and pediatric care shortages, many areas of the United States experience a shortage of mental health providers. Shortages are impacted, in some examples, by alcohol abuse prevalence, substance misuse prevalence, ratio of elderly population (e.g., over age 64), and ratio of youth population (e.g., under age 18). Provider shortages often result in higher costs, exacerbating affordability issues and leading to inappropriate care settings and lower preventative screening rates. For example, HPSA areas typically see an increased infant mortality rate (IMR) and/or low birth weight (LBW) rate.

The inventors recognized a need to factor in these out-of-pocket expenses to demonstrate to plan payers, such as employers, the impact of benefits package selections on subscriber affordability.

SUMMARY OF ILLUSTRATIVE EMBODIMENTS

Health outcomes are impacted by a variety of factors including social & economic factors (e.g., education, employment, income, community safety, family and social support, etc.), personal behavior (e.g., smoking, alcohol, substance misuse, diet, exercise, unsafe sex, etc.), access to needed healthcare providers (e.g., physicians, specialists, counselors, psychologists, etc.), and environmental factors (e.g., air quality, water quality, housing quality, transit availability, etc.). The University of Wisconsin combined some elements of these health care outcome factors into an Area Deprivation Index (ADI) used to compare census block groups (e.g., neighborhoods) by relative socioeconomic disadvantage on a scale from 1 to 100. The ADI may be aggregated into thirds identified, for example, as high ADI risk (e.g., greater than 67), medium ADI risk (e.g., between 34 and 66) and low ADI risk (e.g., less than or equal to 33). Individuals living in high ADI risk areas tend to experience higher utilization of emergency room services and lower utilization of preventative services. The high ADI risk areas are associated with increased risk for a number of chronic conditions (e.g., diabetes, hypertension, asthma) as well as higher tobacco consumption.

To improve healthcare outcomes, the health care needs of a subscriber population, in some implementations, are analyzed to estimate utilization (e.g., number of visits, costs for health care services, medications, and equipment, etc.) and calculate estimated costs to the subscribers for the utilization. The healthcare costs, including both subscriber contribution costs to insurance as well as out-of-pocket costs associated with utilization, may then be compared to subscriber income to analyze affordability to the subscriber.

In some implementations, costs, healthcare utilization, and/or affordability are analyzed in view of census data to estimate impact to the subscribers based on the region in which they live. Further, provider availability may be analyzed to model impacts of accessibility on costs and/or availability of care.

In some implementations, plan payers, such as employers, are given access to an interactive portal to review information regarding affordability, payer accessibility, and/or ADI factors in view of location(s) of employees. Portions of the information, for example, may be provided in the form of a color-coded map, illustrating geographic variances in health and wellness outcomes. Portions of the information, in another example, may be provided in one or more comparison tables, for example comparing affordability metrics and/or health and wellness factors based on income ranges. Further, affordability metrics may be compared to peer metrics (e.g., by location, industry, size, etc.) for competitive offerings analysis.

The foregoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or

US 12,586,096 B2

Figure 1:
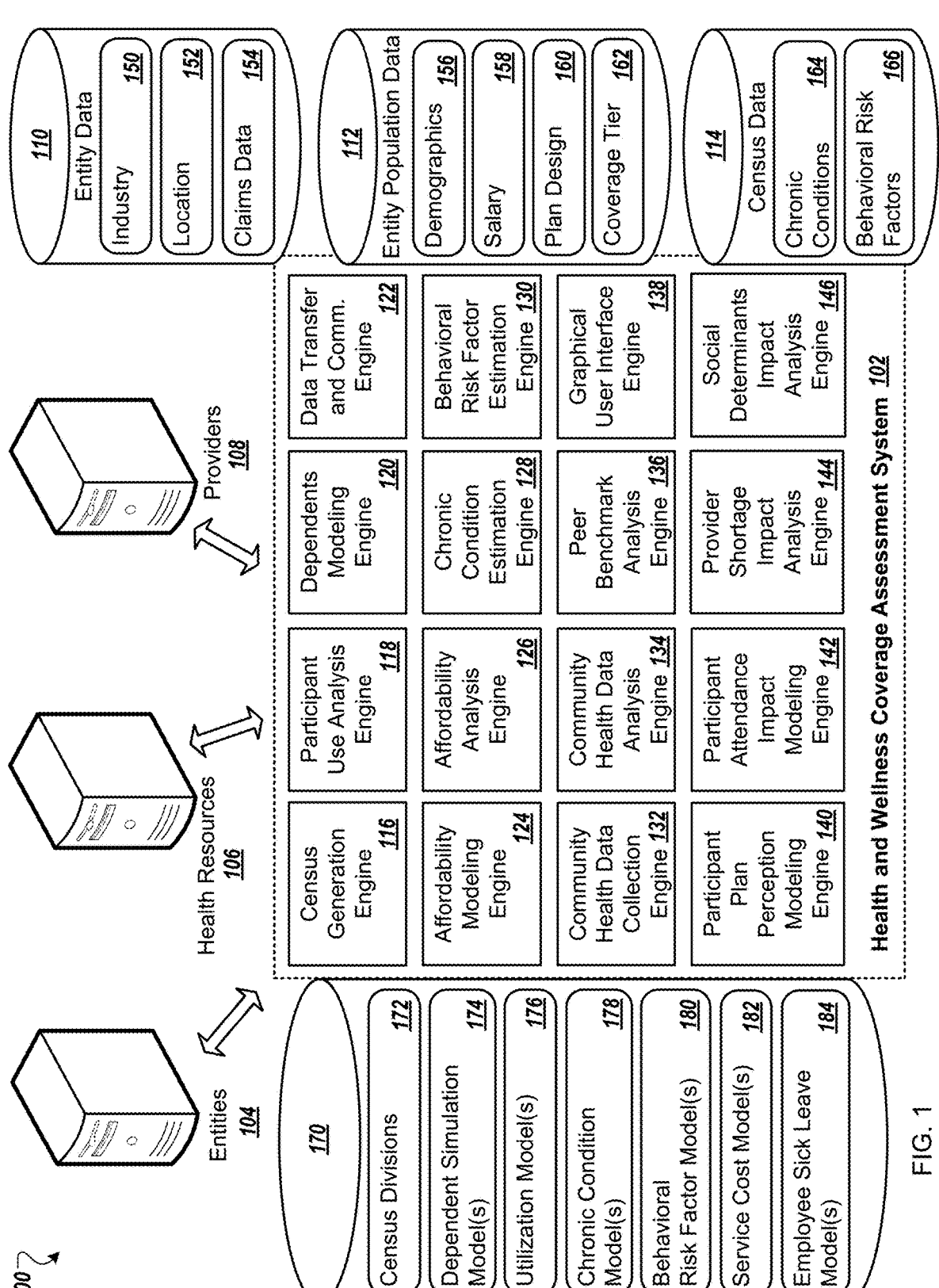
Figure 2A:
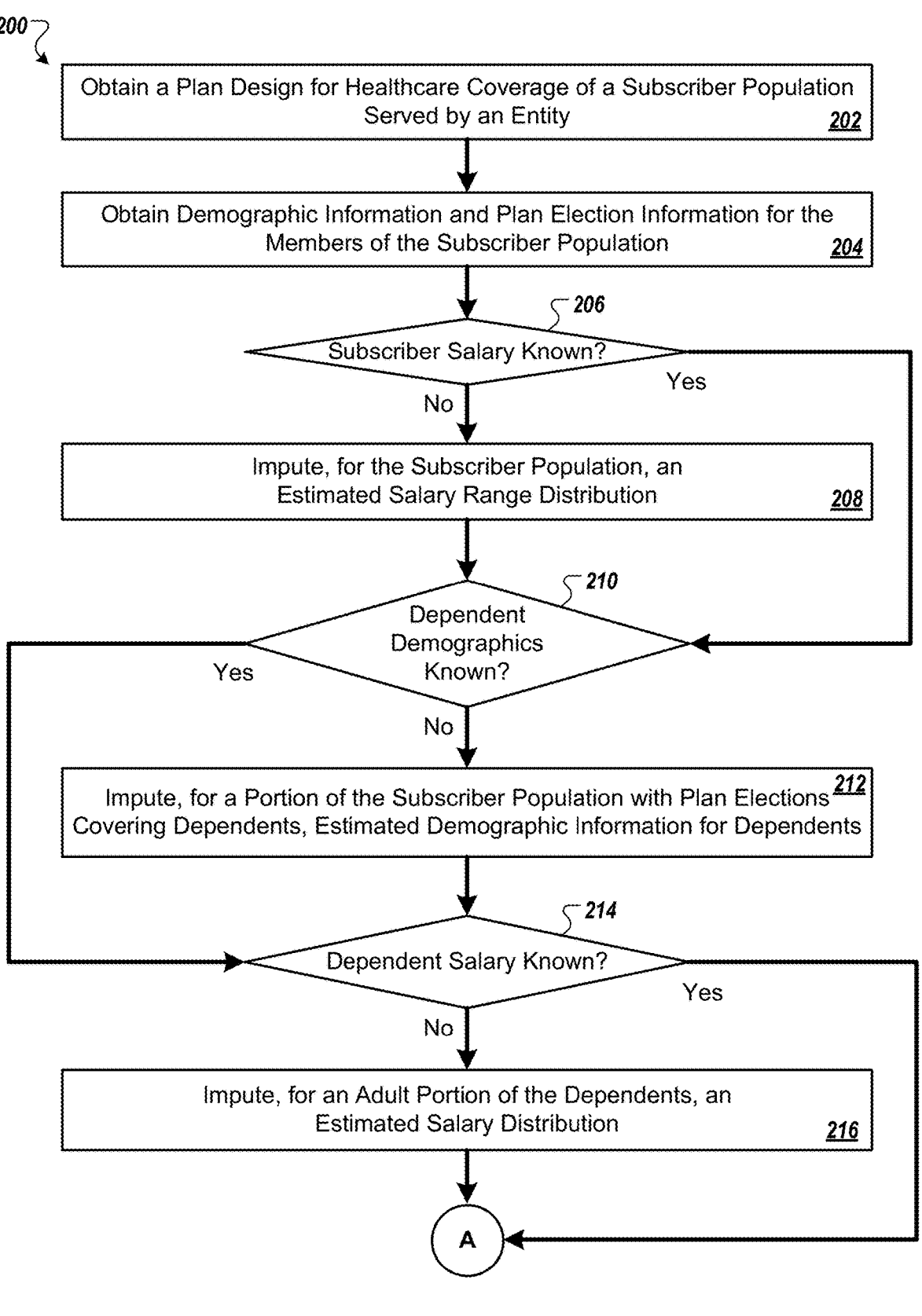
Figure 2B:
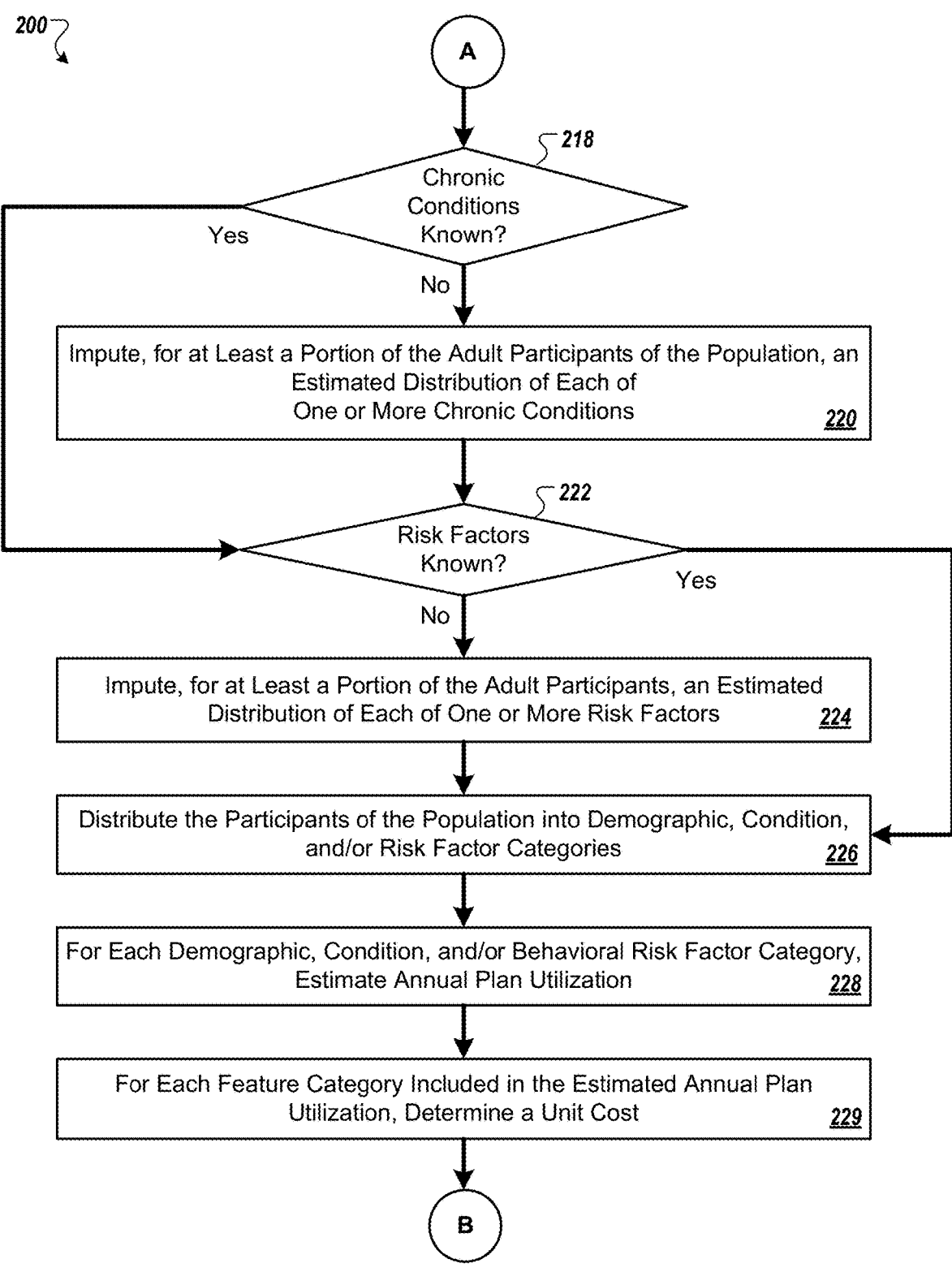
Figure 2C:
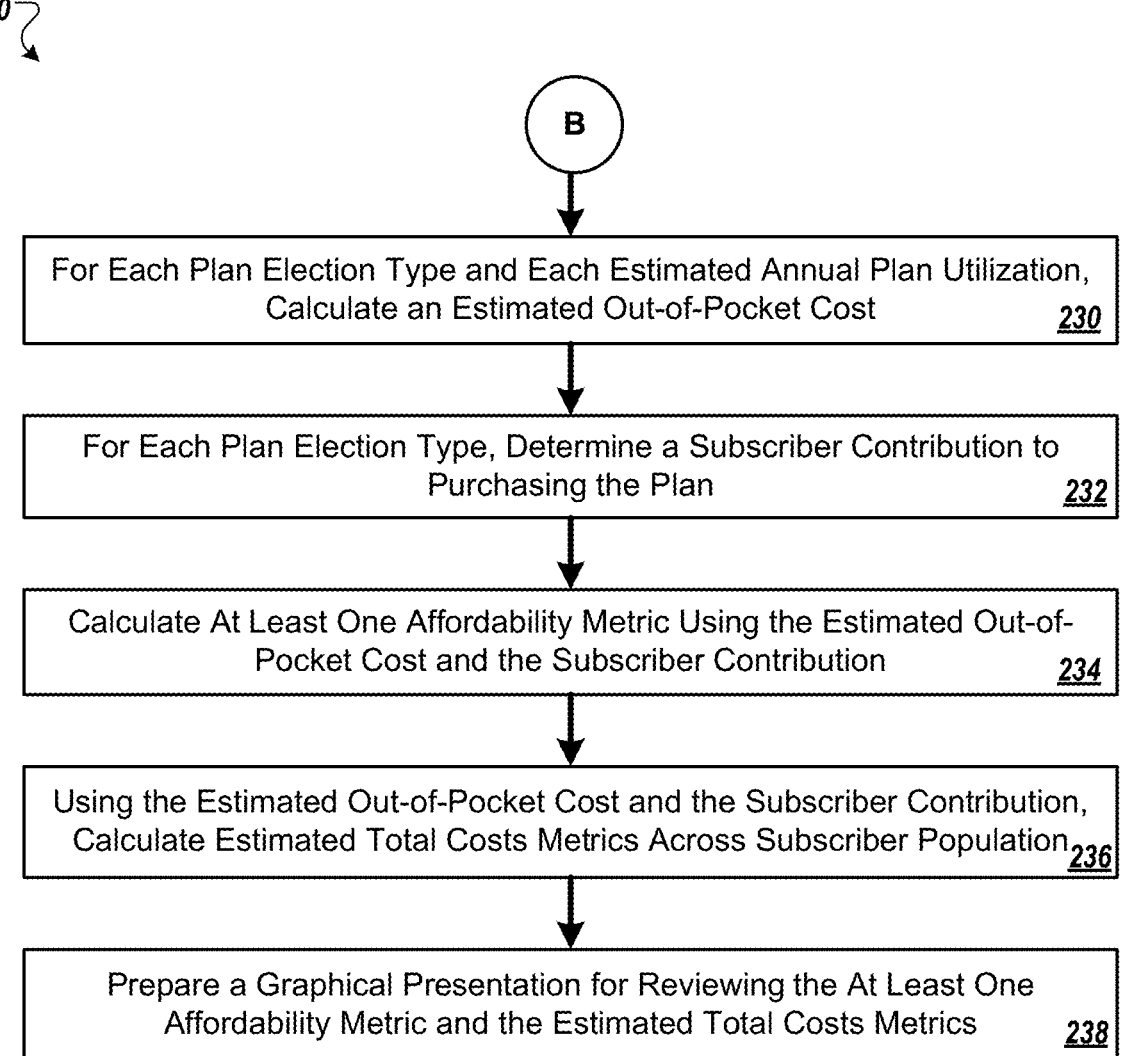
Figure 3A:
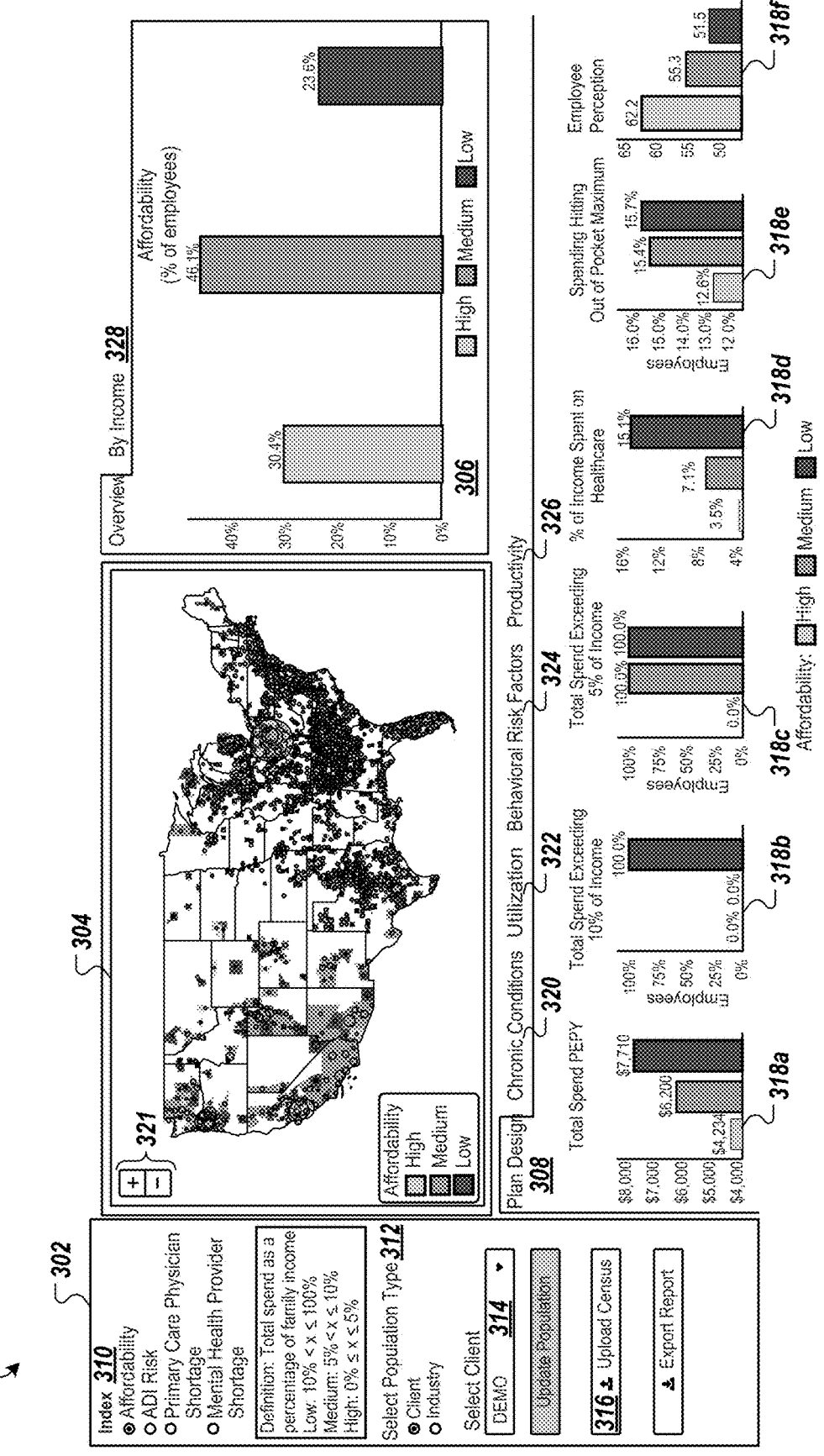
Figure 3B:
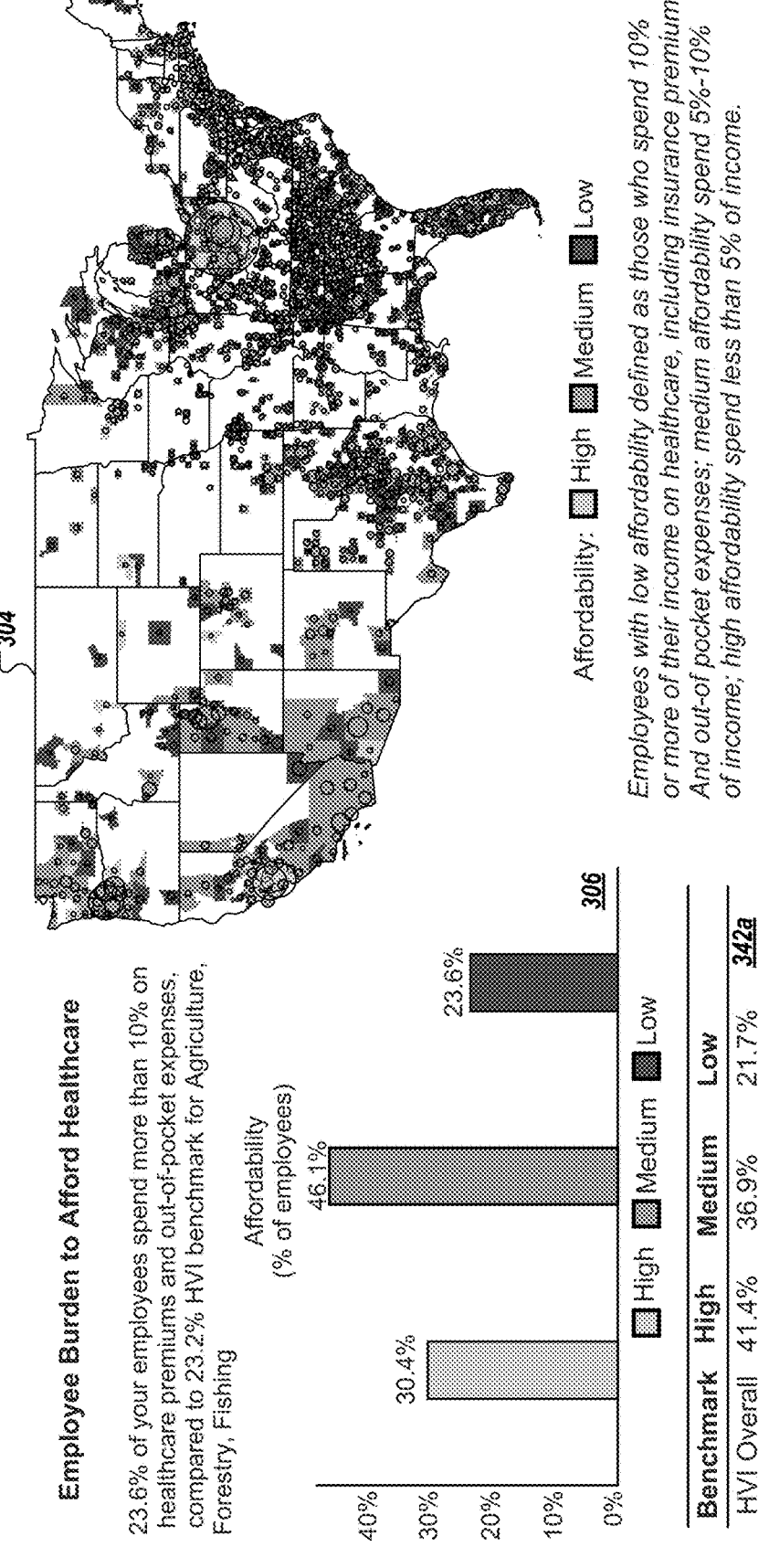
Figure 3C:
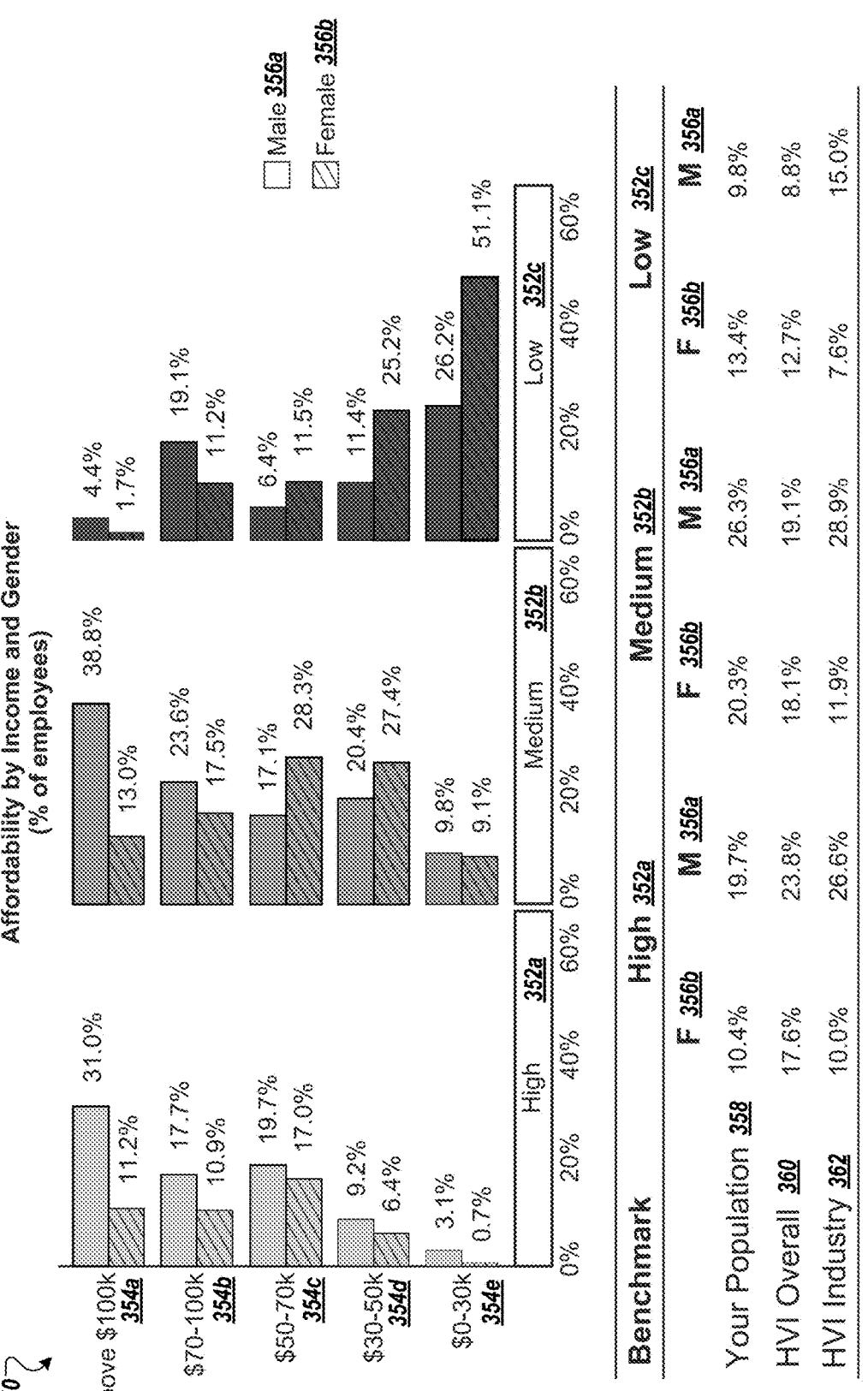
Figure 5A:
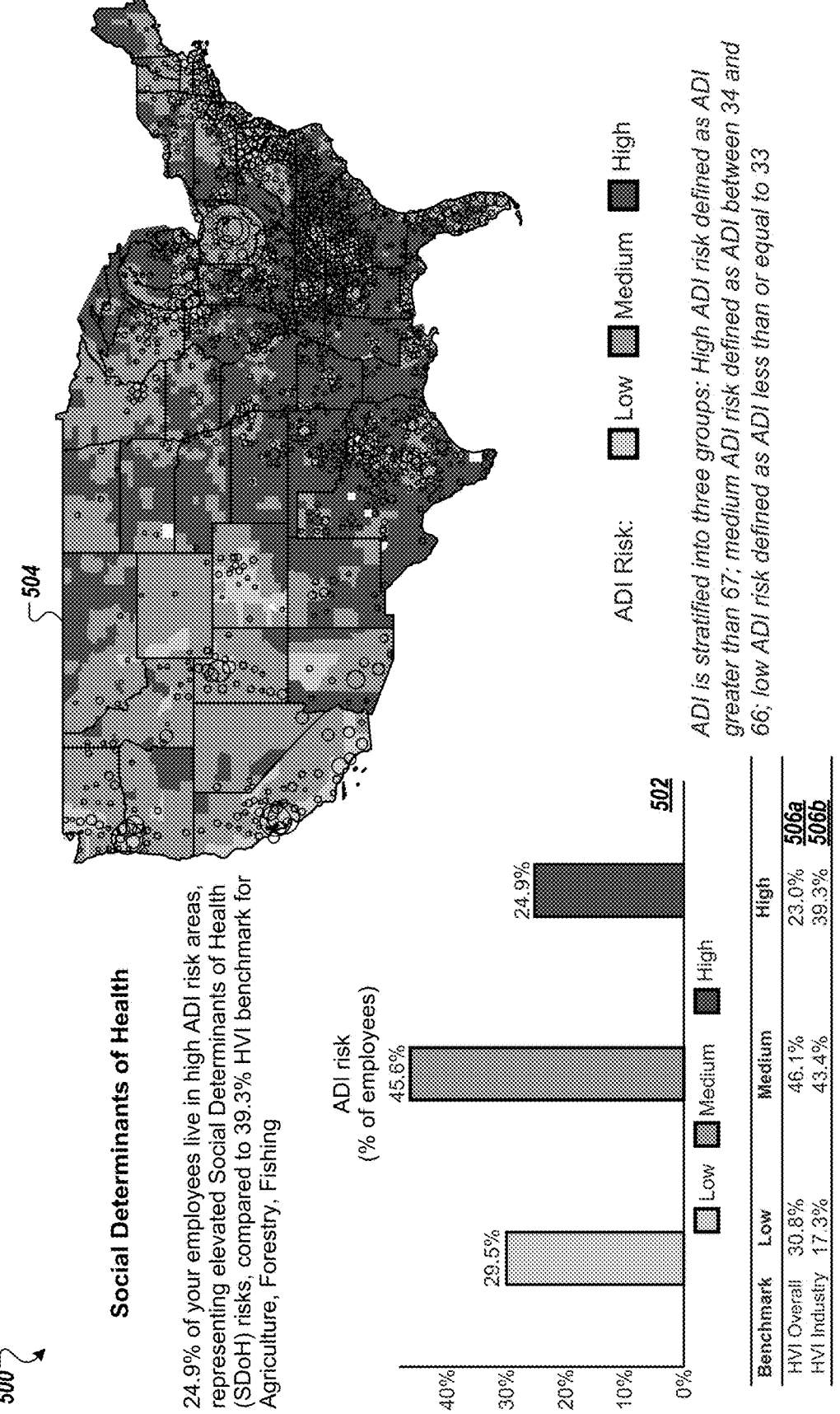
Figure 5B:
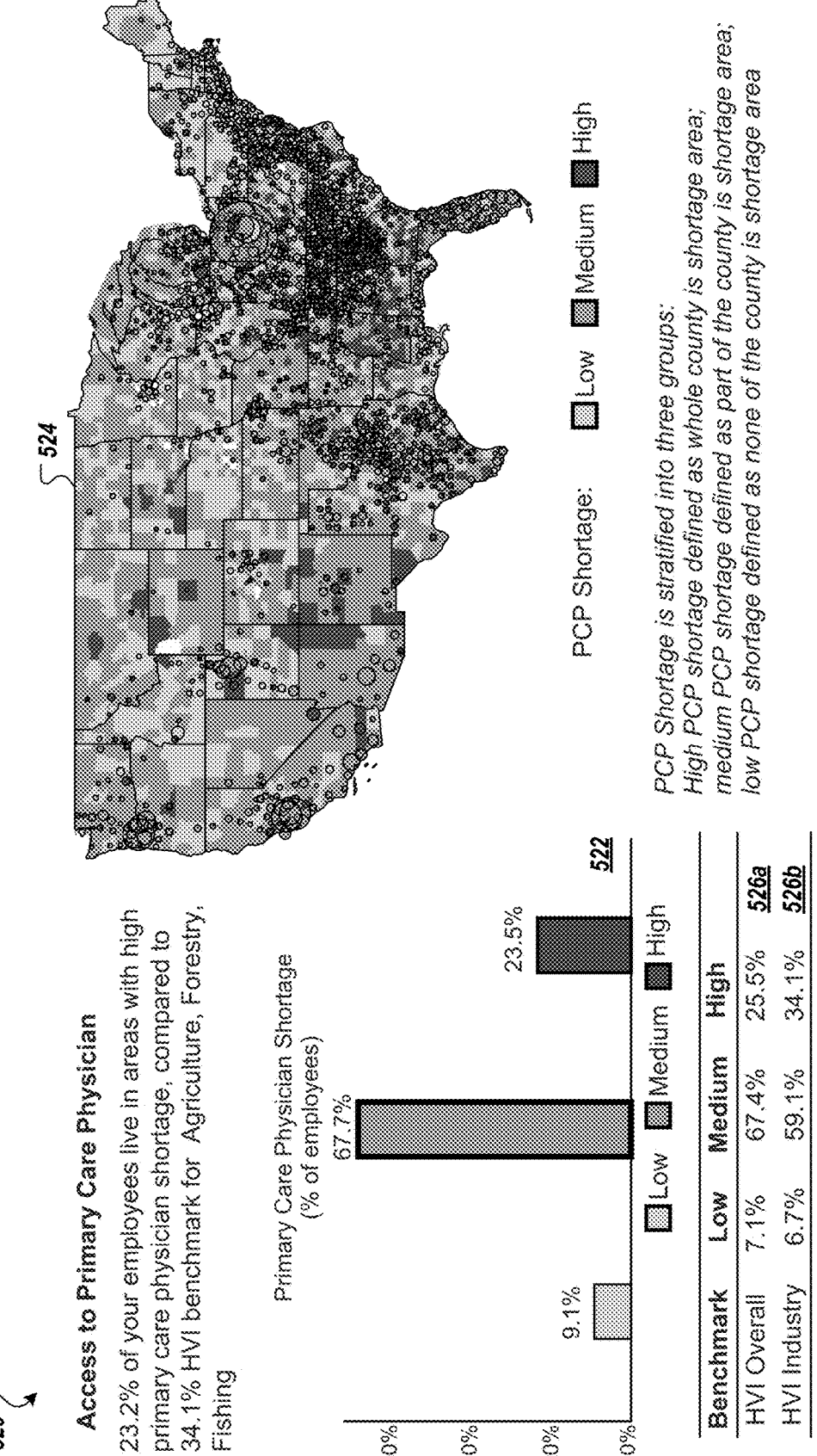
Figure 5C:
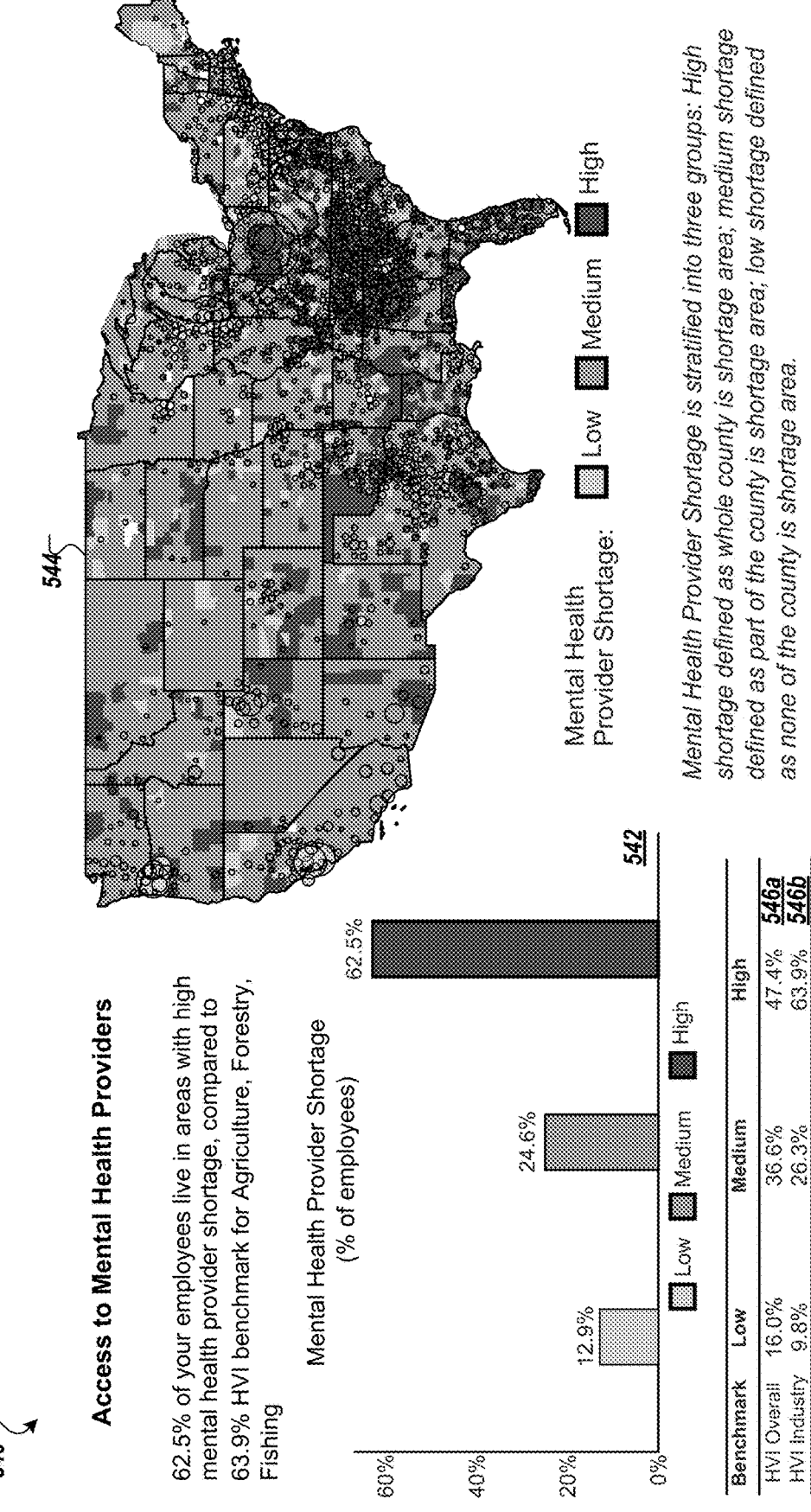
Figure 6:
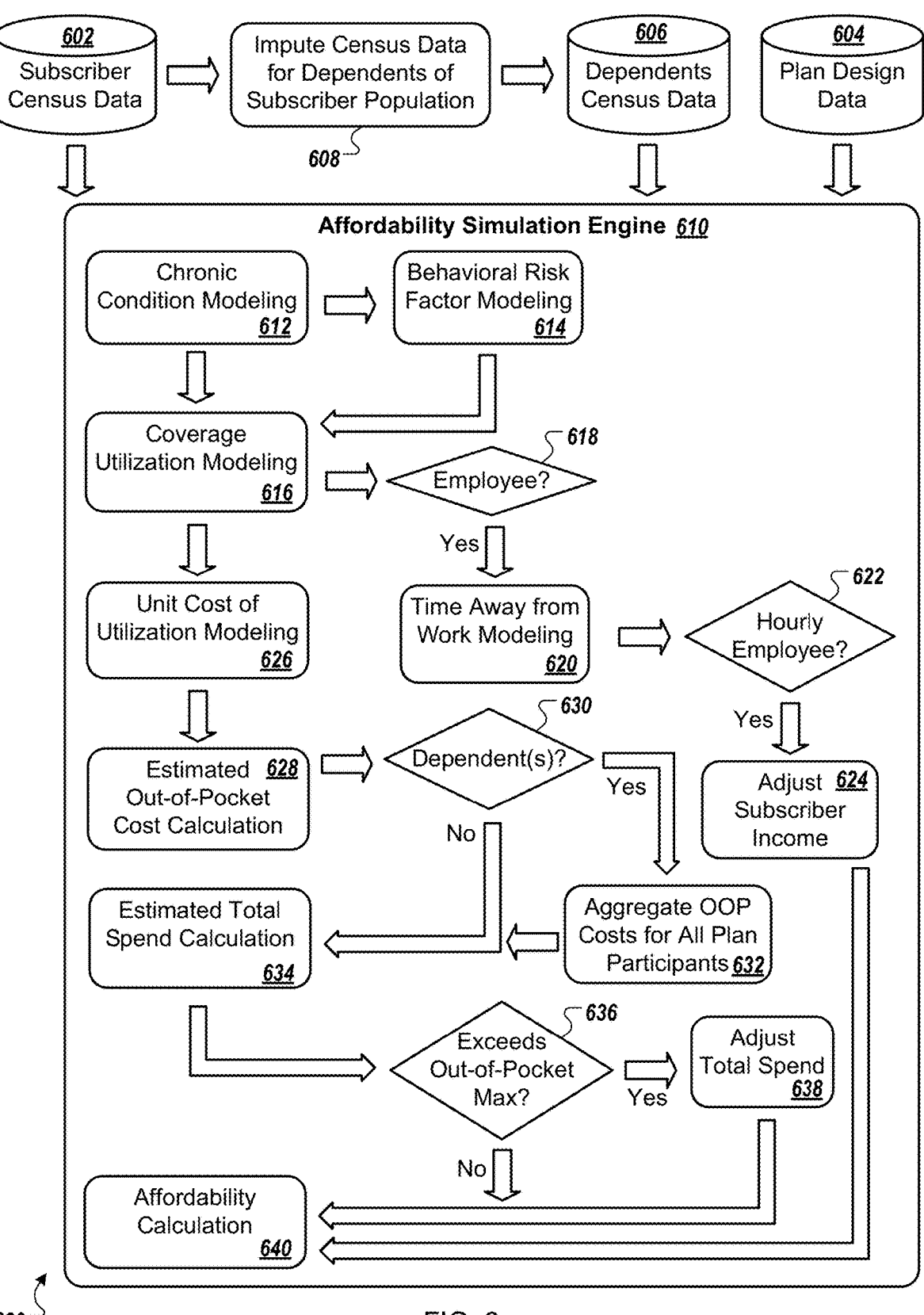
Figure 7A:
Figure 7B:
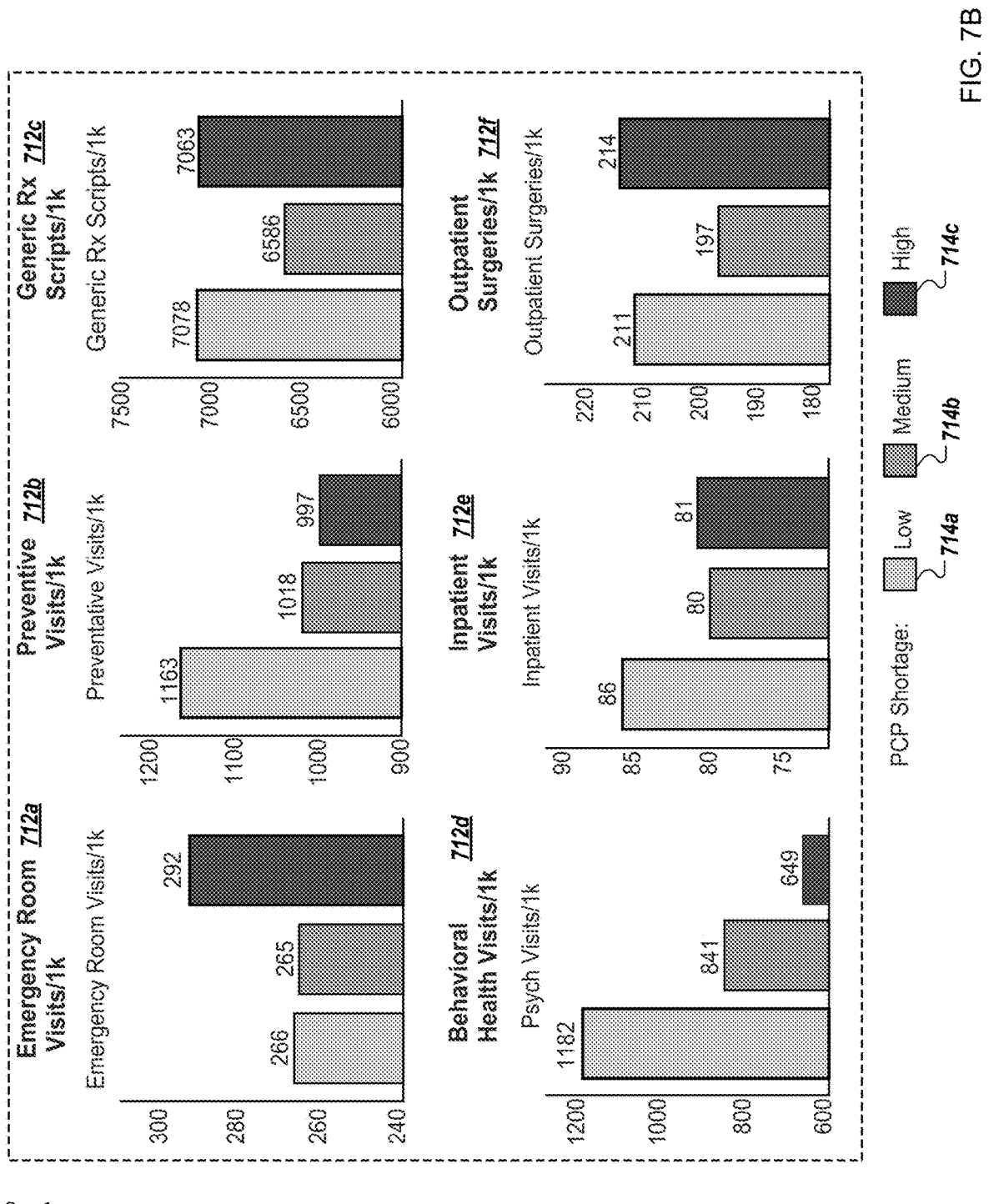
Figure 8B:
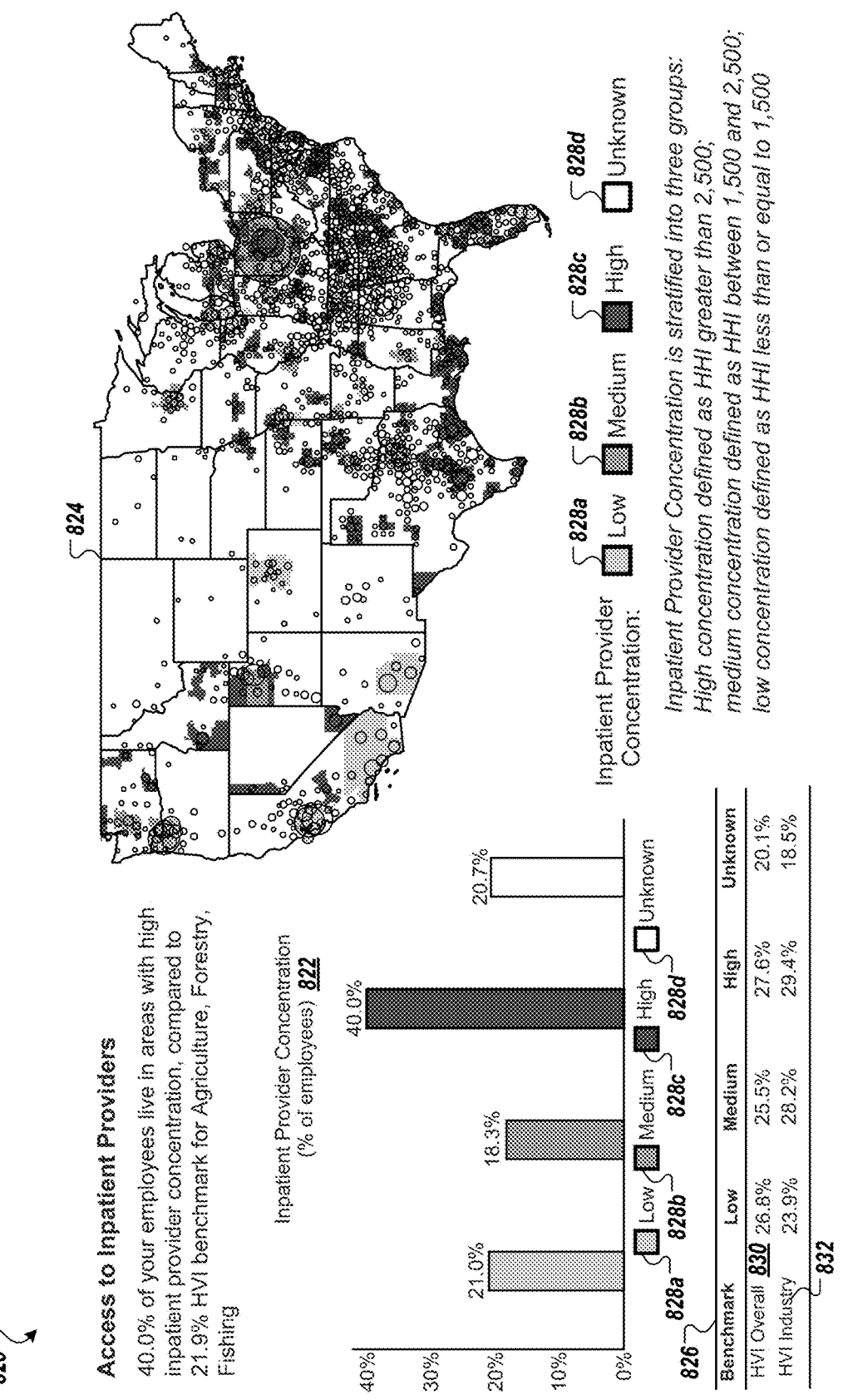

3 more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIG. 1 is a block diagram of an example system and environment to estimating health and wellness affordability and availability to a population;

FIG. 2A through FIG. 2C illustrate a flow chart of an example method for analyzing a subscriber population in view of health and wellness affordability;

FIG. 3A through FIG. 3C illustrate example user interface and output screens for reviewing affordability data;

FIG. 4 illustrates an example output screen providing an overview regarding analysis made on an employee population of an agricultural, forestry, or fishing company;

FIG. 5A through FIG. 5C illustrate example output screens for reviewing geographic healthcare impacting factor data;

FIG. 6 illustrates an operational diagram of an example process for analyzing an employee population in view of health and wellness affordability;

FIG. 7A is an example GUI presentation portraying graphical estimates of behavioral risk factors across risk categories of a population;

FIG. 7B is an example GUI presentation portraying graphical estimates of medical category utilization across risk categories of a population; and FIG. 8A and FIG. 8B illustrate example output screens for reviewing geographic healthcare impacting factor data involving medical provider metrics.

DETAILED DESCRIPTION OF ILLUSTRATIVE EMBODIMENTS

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

FIG. 1 is a block diagram of an example health and wellness coverages assessment system 102 and environment 100 for estimating health and wellness affordability and availability to a population. In some implementations, the environment 100 includes a set of entities 104 connecting to the health and wellness coverage assessment system 102 for analyzing subscription offerings provided to a population of the organization. The system 102 may access information from one or more health resources 106 to derive basic metrics related to geographic location(s) of the entity's population and/or from one or more providers 108 (e.g., insurance providers) for details regarding plan designs offered to the population.

In some implementations, the system 102 obtains information regarding one of the entities 104 for analyzing health and wellness coverage of a population associated with the entity 104 (e.g., employees, members of an organization, etc.) referred to generally herein as "subscribers." The information, in some examples, may be obtained by a graphical user interface (GUI) engine 138 via an interactive GUI and/or from a data transfer and communications engine 122 (e.g., using file transfer protocol (FTP), an application programming interface (API), a secure sockets layer (SSL) connection, or other data transfer connection with one of the entities 104). The information, in one example, may include entity data 110 regarding the entity 104 such as, in some examples, an industry 150 of the entity or a type of entity 104 (e.g., governmental, educational, etc.), one or more locations 152 of the entity 104 (e.g., locations of business, location of residences, etc.) and/or a set of claims data 154 for subscribers affiliated with (e.g., employed by, belonging to, etc.) the entity 104. In another example, the information may include entity population data 112 such as, in some examples, demographics 156 (e.g., age, gender, race, at least a partial address, marital status, educational level, etc.) and/or salary or salary range 158 (or other information for imputing salary, such as job title) for each member of the population. The population data 112 may further include subscription information including a plan design 160 (e.g., employee contribution level, co-pay levels, other out-ofpocket expenses such as deductible levels, etc.), a coverage tier 162 (e.g., individual, individual plus spouse, family, etc.), and/or other identifier of insurance plan (e.g., plan name, plan code, etc.) with which the plan design information 160 may be obtained (e.g., from the providers 108).

In some implementations, the system 102 obtains census data 114 from one or more health resources 106. The census data 114, for example, may identify regional propensity for chronic conditions 164 (e.g., skin cancer, other cancers, arthritis, asthma, stroke, myocardial infarction, diabetes, kidney disease, and/or mental health disorders, etc.) and/or behavioral risk factors 166 (e.g., heavy alcohol consumption, tobacco consumption, poor nutrition, and/or obesity, etc.). The census data 114, for example, may be collected from one or more databases, data stores, and/or servers. The census data 114, in some examples, may be collected from one or more governmental sources, educational sources, medical sources, and/or research sources. A community health data collection engine 132 may collect at least a portion of the census data 114.

In some implementations, a census generation engine 116 analyzes the entity population data 112 to distribute the population into census divisions. The census divisions, for example, may be used to fine-tune healthcare usage estimates. Females of childbearing age, for example, may incur certain pregnancy-related expenses, on average, while males near retirement age will have different typical expenses due to certain common conditions and/or ailments. Thus, in dividing the population data 112 into one or more categorizations, better estimates may be obtained. The census generation engine 116 may divide the participant (e.g., subscribers, spouses, dependents) into categorized divisions that reflect demographic features of the participants as well as health aspects of the participants (e.g., chronic conditions 164 and/or behavioral risk factors 166). For example, the demographic categories may include salary, dependent count, age, gender, spousal employment, income, each of one or more of the chronic conditions 164 and/or each of one or more of the behavioral risk factors 166. Further, the census divisions may include plan election divisions based on different offerings included in the plan design 160 (e.g., coverage tier, plan subgroup, etc.). Additionally, each category may include multiple divisions to which subscribers are assigned. For example, the salary category may include five, ten, fifteen, or more divisions that each reflect salary ranges between $0 and more than $200,000. Similarly, an age category may include divisions that each reflect a particular range of ages. In some implementations, the census generation engine 116 assigns each participant to a division within each demographic category, and the participant counts within each of the divisions are saved along with the census divisions in a data store 170 as census divisions 172.

In some embodiments, for those members of the population having a coverage tier 162 indicating a spouse, child (ren), and/or dependent(s), the census generation engine 116 includes one or more dependent census divisions 172. If the demographics 156 of the entity population data 112 includes gender and age of spouse and/or each child covered by the plan design 160, the actual census divisions may be known. Otherwise, the census generation engine 116 may obtain imputed gender and age of spouse and/or children through estimations. For example, each spouse may be estimated to be about the same age as the employee (e.g., a member of the same age census division). In some examples, the gender of each spouse may be assumed to follow census data (e.g., obtained from one of the health resources 106 or another resource for local demographics data) or, for simplicity's sake, assumed to be opposite gender. Further, the age and gender of children may be estimated based on local age distributions of children. The ages may be based further in part on parental age (or age plus educational level). In an illustrative example, a probability of children counts may be applied to impute the number of dependents per subscriber having a coverage tier 162 indicating children or spouse plus children.

In some implementations, a dependents modeling engine 120 generates simulated ages and numbers of children per member of the population having a coverage tier 162 indicative of children. The dependents modeling engine 120, for example, may simulate ages and genders of children from a normal distribution ranging from newborn to an estimated maximum age of coverage (e.g., 22, 23, 24, 25, etc.). The dependents modeling engine 120 may apply one or more dependent simulation models 174 to estimate a distribution of dependents for the member population. The dependent simulation model(s) 174, for example, may be trained using a normal distribution for the geographic region, such as a U.S. normal distribution, a U.S. regional normal distribution (e.g., northeast, northwest, Midwest, southeast, south, southwest, northwest, etc.), and/or state, county, and/or municipality normal distributions. The dependent genders, for example, may be distributed generally equally.

In some implementations, a participant use analysis engine 118 obtains the census divisions 172 and analyzes estimated health care utilization of the members of the population. The participant use analysis engine 118 may further analyze estimated health care utilization of the dependents (e.g., spouses and/or children) of the members of the population. The participant use analysis engine 118, for example, may apply one or more utilization models 176 to the census divisions 172 to estimate insurance utilization based on the demographics of the member population. The utilization models 176, in some examples, may model distributions across population divisions for prescription medication usage, physician visits, emergency care visits, hospital stays, physical therapy appointments, counseling sessions, dental visits, eye doctor visits, minor surgical procedures, major surgical procedures, cancer therapies, vaccinations, and/or specialist visits. The utilization models 176, in some embodiments, include utilization models 176 trained to estimate utilization based upon one or more risk factors and/or chronic conditions. The utilization models 176, in some examples, may include gradient boosting machine (GBM) or bagging models, logistic regression models, K-nearest neighbors (KNN) models, other one-class or multi-class support vector machine (SVM) models, other tree-based models such as a decision tree, neural network, deep learning, random forest (RF), multiple regression models, quantile regression, and/or simulation models. The participant use analysis engine 118 may provide, for each census division 172, a utilization profile (e.g., table, vector, etc.) identifying a frequency of use of various categorizations of services and/or various plan features.

In some embodiments, the participant use analysis engine 118 estimates utilization at least in part through analyzing historic claims data 154 of the entity and/or a larger population of entities. Analyzing the historic claims data 154, for example, may include training one or more machine learning classifiers based on demographic, chronic condition, and/or behavioral risk factor information of the corresponding patients of the claims data 154. The chronic conditions, in another example, may be imputed, in part, based on the coding of the claims data 154 (e.g., the medical services themselves may be indicative of a particular type of chronic condition). The machine learning classifiers, for example, may be trained using sets of customized training variables that reflect the demographic census divisions 172 for the entity as well as the chronic conditions 164 and/or behavioral risk factors 166. The machine learning classifiers and/or models, in some examples, may include gradient boosting machine (GBM) or bagging models, logistic regression models, K-nearest neighbors (KNN) models, other one-class or multi-class support vector machine (SVM) models, other tree-based models such as a decision tree, neural network, deep learning, random forest (RF), multiple regression models, quantile regression, and/or simulation models.

In some implementations, a chronic condition estimation engine 128 is used to estimate distribution of chronic conditions among the subscriber population. Further, the chronic condition estimation engine 128 may estimate the distribution of chronic conditions among the dependents (e.g., spouse and/or children). The propensity for chronic conditions and/or behavioral risk factors among the participant population, for example, may be estimated based on common geographic distributions, for example obtained from the health resources 106. In another example, certain chronic conditions among the subscriber population may be derived from claims data 154 supplied by the entity 104. The chronic conditions may include various forms of cancer such as, in some examples, skin cancer, breast cancer, lung cancer, and/or prostate cancer. The chronic conditions, in some examples, include arthritis, asthma, hypertension, stroke, myocardial infarction, chronic obstructive pulmonary disease (COPD), diabetes, kidney disease, epilepsy, one or more women's health disorders, and/or one or more musculoskeletal disorders. In further examples, the chronic conditions may include mental health disorders such as anxiety, depression, opioid misuse, and/or other substance misuse.

The chronic condition estimation engine 128, in some embodiments, applies one or more trained chronic condition models 178 to estimate likely numbers of the subscriber population having each of a set of chronic conditions. The chronic condition models 178, for example, may be trained using distributions of chronic conditions 164 by geography (e.g., country, region, state, county, etc.) and/or demography (e.g., age, sex, etc.). The chronic condition models 178, for example, may be applied, in part, based upon a propensity for the chronic condition among certain industries (e.g., environmental hazards and/or workplace hazards lending to greater incidences of the chronic condition than found on a geographic basis). The training data for the chronic condition models 178, for example, may be obtained in part from the health resources 106. In a particular example, Behavioral Risk Factor Surveillance System (BRFSS) data may be obtained from the U.S. Centers for Disease Control and Prevention (CDC). In another example, the training data may be obtained in part from claims data of a large population (e.g., similar and/or including the claims data 154). For example, patient geography and/or demography may be cross-referenced to claims data encodings (e.g., treatments, prescriptions, services, etc.) indicative of and/or corresponding to certain chronic diseases. In some embodiments, at least a portion of the trained chronic condition models 178 are applied to the claims data 154 to correlate claims data codings to chronic diseases.

In some implementations, a behavioral risk factor estimation engine 130 is used to estimate distribution of behavioral risk factors among the subscriber population. Further, the behavioral risk factor estimation engine 130 may estimate the distribution of behavioral risk factors among the dependents (e.g., spouse and/or children). The behavioral risk factor estimation engine 130, in some embodiments, applies one or more trained behavioral risk factor models 180 to estimate likely numbers of the subscriber population having each of a set of behavioral risk factors. The behavioral risk factors, in some examples, may include heavy alcohol consumption, tobacco consumption, vaping, poor nutrition, poor exercise habits, and/or obesity. The behavioral risk factors may include risk factors typically derived from laboratory results and/or medical testing, such as, in some examples, high cholesterol and/or high blood pressure. The behavioral risk factor models 180, for example, may be trained using demographic distributions of behavioral risk factors 166 by geography (e.g., country, region, state, county, etc.). The behavioral risk factor models 180, for example, may be applied in part based upon a propensity for the condition among certain industries (e.g., obesity being higher in industries having sedentary workers, etc.). The training data for the behavioral risk factor models 180, for example, may be obtained in part from the health resources 106. In a particular example, BRFSS data may be obtained from the CDC. In another example, the training data may be obtained in part from survey data obtained from a subscriber population.

In some implementations, a community health data collection engine 132 collects regional health data from the health resources 106. The community health data collection engine 132, for example, may collect information from the Centers for Disease Control and Prevention (CDC), the Health Resources and Services Administration (HRSA), the Institute for Health Metrics and Evaluation (IHME), the Health Care Cost Institute (HCCI), research organizations, hospitals, medical centers, local (e.g., county or state) survey data, etc. The community health data collection engine 132, in some embodiments, collects data on a periodic basis (e.g., on a known update basis for each of the health resources 106, monthly, weekly, daily, etc.). The community health data collection engine 132 may store the collected information as part of the census data 114 (e.g., regarding chronic conditions 164 and/or behavioral risk factors 166).

In some implementations, a community health data analysis engine 134 analyzes the census data 114 to aggregate, organize, and/or categorize the information collected for application to various subscriber populations. For example, the community health data analysis engine 134 may reformat at least a portion of the collected data so that the census data 114 has a consistent formatting across datasets. Further, the community health data analysis engine 134 may aggregate data sets to produce metrics at varying geographic refinements (e.g., zip code plus 4, 5-digit zip code, town, city, county, municipality, etc.).

In some implementations, an affordability modeling engine 124 models estimated economic impacts of the utilization data generated by the participant use analysis engine 118 to the participants based on the plan design(s) 160. The affordability modeling engine 124, for example, may attribute costs to the various types of utilization (e.g., visits, prescriptions, etc.) and/or the various chronic conditions 164 and/or behavioral risk factors 166. The affordability modeling engine 124, for example, may apply factors of the plan design 160 such as copay amounts to certain types of utilization. The affordability modeling engine 124 may further estimate costs, at least in part, through analyzing historic claims data 154 of the entity and/or a larger population of entities. In illustration, portions of claims unpaid by the insurance coverage and/or claims denied by the insurance provider and thus left as a patient expense may be analyzed. In some embodiments, the affordability modeling engine 124 applies one or more service cost models 182 developed from analyzing historic medical costs (e.g., claims, invoices, etc.). The affordability modeling engine 124, in some embodiments, provides cost modeling data to an affordability analysis engine 126.

In some implementations, the affordability analysis engine 126 applies the salary information 158 and plan design information 160 to the cost modeling data to estimate affordability to various levels of participant categorization (e.g., demographics 156, demographics 156+plan design 160, demographics 156+plan design 160+coverage tier 162, demographics 156+salary 158 (e.g., salary tier, salary band) etc.) of the subscriber population. The affordability estimate, further, may be based, in part, on imputing a spouse salary for multi-member households. In an example, the affordability analysis engine 126 may estimate a percentage of total household income allocated to covering anticipated medical expenses. In another example, the affordability analysis engine 126 may estimate a total annual cost to each participant categorization. The affordability analysis engine 126 may output a set of affordability metrics.

In some implementations, a peer benchmark analysis engine 136 matches a subject entity to a set of peer entities and supplies comparisons in healthcare usage and/or affordability. For example, the peer benchmark analysis engine 136 may provide a comparison of use metrics, cost metrics, and/or attendance metrics between the subscriber population of the subject entity and previously analyzed subscriber populations of the peer entities. The metrics of the previously analyzed subscriber populations, for example, may be combined (e.g., average, median, etc.) to provide a general benchmark metric corresponding to the peer population. In another example, the peer benchmark analysis engine 136 may identify a set of peer entities, determine plan offerings of the peer entities, and determine actual or estimated usage of the offerings (e.g., between various plan designs, coverage tiers, etc.). For example, the plan offerings of each peer entity may be distributed across the subscriber population of the subject entity based on closest similarity between an elected offering of each participant and available offerings of the peer entity. The affordability modeling engine 124 and/or affordability analysis engine 126 may then prepare estimations of costs to the subscribers of the population based on the differing plan features.

The peer population, in some embodiments, is selected by the peer benchmark analysis engine 136 based on organizational similarities between the entity and each of the other entities 104. The similarities, in some examples, can include an industry, a geographic region, an organizational size (e.g., small business, midsized business, large entity, etc.), and/or a type of organization (e.g., public, private, non-profit, governmental, etc.). In another example, the similarities can include similarities in employee base such as an average or median age, an average or median salary, the percentage of female employees, the percentage of employees opting for a family plan, an age distribution (e.g., within a series of ranges), and/or a salary distribution (e.g., within a series of ranges). In a particular example, the perception benchmarking may be drawn from entities with similarities in employee base not diverging from the employer's employee base by more than a threshold (e.g., percentage, value, or logarithmic distribution). In some embodiments, the peer population is drawn from a simple similarity or set of similarities, such as industry. When selecting a broad range of peers, for example, one or more outlier values may be removed when drawing comparisons between entity metrics.

In some implementations, a participant plan perception modeling engine 140 analyzes the plan utilization (e.g., as determined by the participant use analysis engine 118) to identify those features of most value to the participants. The participant plan perception modeling engine 140, for example, may execute one or more artificial intelligence (machine learning) classifiers to analyze the employee utilization in view of the various plan election types of the plan design 160. The machine learning algorithm(s) used by the participant plan perception modeling engine 140, in one example, may be a gradient boosting machine (GBM), which is a tree-based model that uses sets of customized training variables that reflect the census data for the entity (e.g., as determined by the census generation engine) as well as the utilization patterns determined by the participant use analysis engine 118 (e.g., including utilization based on the chronic conditions 164 and/or behavioral risk factors 166). Other types of machine learning algorithms which may be used, in some non-limiting examples, include logistic regression, K-nearest neighbors (KNN), one-class or multi-class support vector machine (SVM), or other tree-based boosting or bagging models such as a decision tree, neural network, deep learning, or random forest (RF). In another example, the participant plan perception modeling engine 140 may take into consideration survey data of the members of the entity identifying levels of satisfaction with various aspects of the plan design 160. The participant plan perception modeling engine 140 may present one or more perception scores related to the perceived value of each plan election type in view of the participant population. The perception scores, for example, may reflect a relative level that each feature of a set of features of the plan design 160 meet the needs of the utilization of the subscriber population. Meeting the needs of membership utilization, for example, may include factoring in a cost differential between a threshold household expenditure (e.g., percentage of income) and an anticipated cost to each subscriber or subscriber category in the census data.

In some implementations, a participant attendance impact modeling engine 142 models the impact of healthcare affordability on the subscriber population in anticipated sick days across the subscriber population. The sick days, for example, may be caused in part due to members of the population avoiding wellness visits, skipping or underdosing prescriptions, postponing recommended procedures, or otherwise making the choice to not spend a portion of income on healthcare, for example, because the affordability metrics estimate that the employee will otherwise struggle to cover the expenses for other requirements such as food and housing. The sick days, further, may be caused, in part, due to the chronic conditions 164 and/or behavioral risk factors 166 which may be mitigated in part through health and wellness support. In some implementations, the participant attendance impact modeling engine 142 applies one or more employee sick leave models 184. The sick leave models 184, for example, may be based in part on external claims data 154 identifying, for example, hospital visits, periodic treatments required by chronic conditions, or other events that are likely to require days off of work. In another example, the sick leave models 184 may be based in part on census data 114, for example identifying metrics related to influenza and pneumonia, each of which can incur an estimated number of sick days based on demographics.

In some implementations, a provider shortage impact analysis engine 144 analyzes health provider regional shortage data, such as the Health Resources and Services Administration (HRSA) data on Health Provider Shortage Areas (HPSAs). The health provider shortage data, for example, may identify primary care health professional shortage areas, inpatient provider shortage areas, and/or mental health professional shortage areas. The data may be analyzed, in some examples, at a zip code regional level and/or a county regional level. The provider shortage impact analysis engine 144 may map the health provider regional shortage data to locations of entity workplaces and/or employee home addresses to generate metrics related to the relative availability of health professionals and/or medical provider offices across the entity's member population.

The provider shortage impact analysis engine 144, in some embodiments, gathers data representing market concentration to generate metrics related to the level of competition (or, conversely, single entity concentration) in a particular region. The data, for example, may be measured using the Herfindahl-Hirschman Index (HHI) standard of measurement for market concentration. The data, in some examples, may be gathered from the Health Care Cost Institute, Inc. (HCCI) and/or the American Hospital Association's (AHA) Annual Survey of Hospitals Database.

In some embodiments, the provider shortage impact analysis engine 144 also captures data related to the cost and/or quality of regional providers. For example, in areas with less competition, the cost associated with visiting a provider may be impacted, increasing the expense of health visits. Additionally, in areas with provider shortages (e.g., rural areas), the overall quality of care may be impacted by stronger medical professional candidates moving to job markets with greater demand and/or greater community amenities than available in certain areas with provider shortages. The cost and/or quality data, in some examples, may be collected from one or more quality ratings organizations, such as regional based quality ratings (e.g., Healthcare Compass MA by Massachusetts Health Quality Partners, Minnesota HealthScores by Minnesota Community Measurement, etc.) and/or national quality ratings (e.g., Care Compare by the Centers for Medicare & Medicaid Services (CMS), the National Committee for Quality Assurance (NCQA) report cards, etc.). The scores may be directly obtained through a ratings organization or calculated based on a number of evaluation criteria (e.g., multiple metrics gathered from one or more quality ratings organizations). In one example, the score may be provided on a scale from 0 to 100, with 50 being a national average provider rating.

In some implementations, a social determinants impact analysis engine 146 analyzes Area Deprivation Index (ADI) data derived from a model created by researchers at The University of Wisconsin. The ADI data, for example, includes factors for domains including education, income, employment, housing, and household characteristics. The social determinants impact analysis engine 146 may aggregate the ADI data to match to geographic information provided by the entity for the subscriber population. The social determinants impact analysis engine 146 may further generate metrics based on the areas of entity workplaces (e.g., in the zip code of each workplace, within an immediate commute range including the immediately surrounding zip codes of each workplace, etc.).

FIG. 2A through FIG. 2C illustrate a flow chart of an example method 200 for a flow chart of an example method for analyzing a subscriber population in view of health and wellness affordability. The method 200, for example, may be performed by the health and wellness coverage assessment system 102 of FIG. 1 on behalf of one of the entities 104.

Turning to FIG. 2A, in some implementations, the method 200 begins with obtaining a plan design for healthcare coverage of a subscriber population served by an entity (202). The information may be obtained from one of the entities 104 of FIG. 1 as entity population data 112 including the plan design 160. The plan design, for example, may include information regarding copays, in-network maximums, out-of-network maximums, and/or subscriber contributions to covering the cost of each election type (e.g., plan tier) of the plan design.

In some implementations, demographic information and plan election information is obtained for members of the subscriber population (204). The plan election information may identify, for each member of the population, a type or tier selection from the plan design. The demographic information, for example, may be the demographics data 156 of the entity population data 112 of FIG. 1. The demographic information may include subscribers as well as, in some embodiments, dependents of certain subscribers (e.g., spouses and/or children) who may be covered by the plan election.

In some implementations, if subscriber salaries are not known (206), an estimated salary range distribution is imputed for the subscriber population (208). The subscriber salary information, or salary range information, may be identified by the entity (e.g., as salary data 158 of the entity population data 112 of FIG. 1). If not, salaries may be imputed based on other entity data, such as, in some examples, ages of the subscribers (e.g., estimated experience levels), job titles or positions of the subscribers, industry of the entity (e.g., by estimating using peer organization salary ranges, by published data regarding salary levels of positions within industry), and/or employee addresses (e.g., zip code or zip code plus 4 pointing to typical income levels of area, address pointing to local minimum wage, etc.).

In some implementations, if dependent demographics are not known (210), estimated dependent demographic information is imputed for a portion of the subscriber population having plan elections covering dependents (212). Dependent demographic information, for example, may be estimated using the dependents modeling engine 120 of FIG. 1 (e.g., through applying one or more of the dependent simulation models 174). Age and gender of each spouse for subscriber plus spouse and subscriber plus family style plan elections may be estimated based on demographics of the corresponding subscribers. Further, ages, genders, and counts of children for each subscriber having a subscriber plus family style plan election or subscriber plus children style plan election may be estimated based on subscriber demographics such as age and/or home address (e.g., geographic region).

In some implementations, if the salary for each adult dependent (e.g., spouse or significant other) is unknown (214), in some implementations, an estimated salary distribution is imputed for the adult portion of the dependents (216). The salaries, for example, may be estimated based, in part, on employee addresses (e.g., zip code or zip code plus 4 pointing to typical income levels of area, address pointing to local minimum wage, etc.).

Turning to FIG. 2B, in some implementations, if chronic conditions of the subscriber population and/or the dependent population are unknown (218), an estimated distribution of each of one or more chronic conditions is imputed for at least a portion of the adult participants of the population (220). For example, a distribution of chronic conditions may be imputed across both subscriber population and the known or imputed significant others and/or spouses. Further, in some embodiments, a distribution of chronic conditions may be imputed for the known or imputed children. The chronic condition estimation engine 128 of FIG. 1, for example, may impute chronic conditions. The chronic conditions may be estimated using the chronic condition model(s) 178 of FIG. 1 and/or the conditions data 164 of the census data 114 of FIG. 1.

In some implementations, if behavioral risk factors associated with the subscriber population are unknown (222), an estimated distribution of each of one or more behavioral risk factors may be imputed for at least a portion of the adult participants (224). The behavioral risk factor estimation engine 130 of FIG. 1, for example, may be used to impute distributions of behavioral risk factors. The behavioral risk factors may be estimated using the behavioral risk factor model(s) 180 and/or the behavioral risk factors data 166 of the census data 114 of FIG. 1.

In some implementations, participants of the population are distributed into demographic, condition, and/or risk factor categories (226). For example, the census generation engine 116 may distribute the participants into the census divisions 172, as described in relation to FIG. 1. The categories, for example, may be based at least in part on a demographic population distribution and/or a health factor (e.g., chronic conditions and/or behavioral risk factors) population distribution of the entity's participants. For example, to categorize based on a particular chronic condition or a particular behavioral risk factor, the participant population may require at least a threshold number and/or percentage of subscribers exhibiting that particular health factor. Further, the divisions in demographics, such as age and/or salary, may be defined in part based on the ranges of the particular participant population. For each category or division, a count of the participants within the category or division may be calculated as well.

In some implementations, an estimated annual plan utilization is determined for each demographic, condition, and/or behavioral risk factor category of the census (228). The annual plan utilization, for example, may be estimated by the participant use analysis engine 118 as described in relation to FIG. 1. The factors considered in the annual plan utilization, in some examples, may depend in part upon features selected for analysis by the entity and/or features of the plan design. The annual plan utilization, for example, may include utilization estimates (e.g., counts of uses) for each of a variety of features (e.g., number of physician visits, number of specialist visits, number of out-of-network visits, number of in-network visits, number of prescription fills, etc.), each feature potentially incurring an out-of-pocket cost, such as a copay.

In some implementations, for each feature category included in the estimated annual plan utilization, a unit cost is determined (229). For example, the corresponding copay values may be determined for each covered feature category of each feature type (e.g., type of service, type of pharmaceutical, and/or type of medical supply). Certain feature categories, in some embodiments, include an additional designation, such as in-network versus out-of-network, such that the same feature (e.g., physician visit) may include two or more categories (e.g., in-network physician visit and out-of-network physician visit).

In some implementations, an estimated out-of-pocket cost is calculated for each plan election type and each estimated annual plan utilization (230). For example, for each demographic and/or health factor census division for which an estimated annual plan utilization was estimated, the estimated out-of-pocket cost to participants may be calculated on a sub-division basis according to plan election type. Calculating the estimated out-of-pocket cost, for example, includes aggregating unit costs of the counts of covered features. Further, the estimated out-of-pocket cost may include estimated expenses for one or more features not covered by the plan election type, such as chiropractic adjustments exceeding a designated cap. As described in relation to FIG. 1, the affordability modeling engine 124 may model costs based on the estimated plan utilization.

Turning to FIG. 2C, in some implementations, a subscriber contribution to purchasing the plan is determined for each plan election type (232). The subscriber contribution, for example, may be identified from the plan design data 160 provided by the entity 104 of FIG. 1. This portion of subscriber cost, for example, is the amount of money annually deducted from the subscriber's paycheck to cover a portion of the cost of health insurance.

In some implementations, at least one affordability metric is calculated using the estimated out-of-pocket cost and the subscriber contribution (234). The affordability metrics, for example, may be calculated for each salary range, each plan election type, and/or each estimated annual plan utilization. In some embodiments, more granular (e.g., by census division such as demographic, chronic condition, and/or behavioral risk factor division) affordability metrics may be aggregated to obtain more general affordability metrics. The affordability analysis engine 126 of FIG. 1, for example, may calculate the affordability metrics.

In some implementations, estimated total costs metrics may be calculated across the subscriber populating using the estimated out-of-pocket cost and the subscriber contribution (236). The total costs metrics, for example, may be calculated for each plan election type, each demographic division of the subscriber population (e.g., age, geography, etc.) and/or each estimated annual plan utilization. In some embodiments, more granular (e.g., by census division such as demographic, chronic condition, and/or behavioral risk factor division) total expense estimates may be aggregated to obtain more general total expense estimates. The affordability analysis engine 126 of FIG. 1, for example, may calculate the total cost metrics.

In some implementations, a graphical presentation is prepared for reviewing at least one affordability metric and the estimated total costs metrics (238). The graphical user interface engine 138, for example, may prepare the graphical presentation for review by a representative of one of the entities 104. The graphical presentation, for example, may include a portion of the information presented in the screenshots illustrated in FIG. 3A through FIG. 3C. In another example, the metrics presented may include affordability information presented in FIG. 4.

Although described as a particular set of operations, in other embodiments, the method 200 may include more or fewer operations. For example, in some implementations, if chronic conditions are not known (218), they may be derived in part through analysis of historic claims data for the subscriber population. Although described as a particular series of operations, in other embodiments, certain operations of the method 200 may occur in a different order and/or concurrently. For example, the subscriber contribution may be determined (232) at any point after obtaining plan election information (204). Other modifications of the method 200 are possible while remaining within the scope and spirit of the disclosure.

FIG. 3A and FIG. 3B illustrate example graphical user interface presentations for presenting affordability metrics, such as those developed through the method 200. The graphical user interface engine 138 of FIG. 1, for example, may generate the user interface presentations of FIG. 3A and FIG. 3B using information derived by other components of the health and wellness coverage assessment system 102.

Turning to FIG. 3A, an example GUI presentation 300 includes a settings menu 302, an affordability heat map 304, an affordability overview presentation 306, and an afford-ability break-down presentation 308. In the GUI presenta-tion 300, affordability is divided into three color-coded bands: "high" (e.g., light peach), "medium" (e.g., salmon), and "low" (e.g., red). A message in the settings menu 302 notes that the breakdown for the affordability bands is based on "total spend as a percentage of family income" and defined as Low: 10%<x≤100%; Medium: 5%<x≤10% and High: 0%≤x≤5%.

As illustrated in the settings menu 302, multiple indices 310 are provided for selection: affordability; ADI risk; primary care physician shortage; and mental health provider shortage. Additional indices may include, in some examples, quality of healthcare providers (e.g., based on ratings, grades, etc.), catastrophic risk(s) (e.g., flood, tornado, hur-ricane, earthquake, etc.), and/or environmental risk(s) (e.g., wildfires, air pollution, water pollution, etc.). In other embodiments, further indications may include behavioral risk factor levels (e.g., based on geography/neighborhood), chronic condition risk (e.g., based on geography/neighbor-hood), and/or violence risk (e.g., based on geography/neighborhood). In further embodiments, indications may be broken down by demographic divisions such as, in some examples, gender, military veteran status, and/or age ranges.

The settings menu 302 indicates that a population type 312 may be selected as either client or industry. Further, a drop-down menu 314 provides the opportunity to select a particular client or industry, depending upon the category currently selected. As illustrated the client category is selected, and the client presented is "DEMO." If an actual client is selected, in some implementations, census data may be uploaded regarding the client's member population via an upload census control 316. The census data uploaded via the upload census control 316, for example, may include any of the entity population data 112 as described in relation to FIG. 1.

Turning to the overview presentation 306 in the top right corner of the GUI presentation 300, the affordability metrics of percentage of employees of the selected client in each affordability band (low, medium, high) are presented in a bar graph. As illustrated, 30.4% are in the high affordability category (e.g., total spend as a percentage of family income is less than or equal to 5%), 46.1% of the employees are in the medium affordability category (e.g., total spend as a percentage of family income is greater than 5% but less than or equal to 10%), and 23.6% of the employees are in the low affordability category (e.g., total spend as a percentage of family income is greater than 10%).

Further affordability metrics are presented in the afford-ability break-down presentation 308 at the bottom of the example GUI presentation 300. The estimates illustrated in the break-down presentation 308, for example, may be an average, median, weighted average, or other aggregate value representing a typical estimated expenditure per household in each of the three categories. A first bar graph 318a presents an estimated total spend per employee per year (PEPY). As illustrated, the total spend PEPY for the three categories is $4,234 for those categorized as having a high affordability rating, $6,200 for those categorized as having a medium affordability rating, and $7,710 for those catego-rized as having a low affordability rating. A second bar graph 318b presents an estimated total spend for employees in each affordability category exceeding 10% of income (high affordability at 0%, medium affordability at 0%, and low affordability at 100%). A third bar graph 318c presents an estimated total spend for employees in each affordability category exceeding 5% of income (high affordability at 0%, medium affordability at 100%, and low affordability at 100%). A fourth bar graph 318d presents a typical percent-age of income spent on healthcare by employees in each affordability range (high affordability at 3.5%, medium affordability at 7.1%, and low affordability at 15.1%). A fifth bar graph 318e presents an estimated percentage of employ-ees in each affordability category reaching out of pocket maximum for the year (high affordability 12.6%, medium affordability 15.4%, low affordability 15.7%). A sixth bar graph 318f presents an estimated employee perception score for employees in each affordability category (high afford-ability 62.2, medium affordability 55.3, low affordability 51.5). The perception scores, for example, may have been derived as described in relation to the participant plan perception modeling engine 140 of FIG. 1.

Turning to the affordability heat map 304 of the example GUI presentation 300, a geographic distribution of employ-ees is color-coded as bubbles of affordability levels. The size of each of the bubbles, for example, may denote a proportion of the subscriber population residing within the area iden-tified by the bubble. As illustrated, for example, employees in both Washington state and California generally enjoy high affordability, according to the color-coded graph, while much of the low affordability is concentrated in the south and south-west of the country. Further, the affordability heat map 304 includes certain shaded regions over which one or more bubbles are located. The shaded areas represent shapes of counties in which the subscribers reside. In zooming into a particular area (e.g., state or portion thereof, etc.), counties underlying the color-coded bubbles may be more recogniz-able. The heat map 304 may include zoom controls 321, allowing a representative of the client selected via the drop-down menu 314 to review varying levels of granularity at the geographic level.

Turning to FIG. 3B, in an example GUI presentation 340, a static version of the heat map 304 is presented to the right of the overview presentation 306 of FIG. 3A. Beneath the overview presentation 306, benchmark comparison metrics 342 are presented, including an overall benchmark afford-ability metric set 342a (high affordability 41.4%, medium affordability 36.9%, and low affordability 21.7%) and an industry affordability metric set 342b (high affordability 36.2%, medium affordability 40.6%, and low affordability 23.2%). The benchmark affordability metric sets 342, for example, may have been generated by the peer benchmark analysis engine 136 of FIG. 1. The overall benchmark, for example, may take into account all of the entities 104 analyzed by the health and wellness coverage assessment system 102, while the industry benchmark may include each entity 104 matching the industry of the subject client. The benchmark metrics, for example, may be aligned with a health vulnerability index (HVI) assigning classifications to strata of healthcare users.

Turning to FIG. 3C, an affordability break-down by income and by gender is illustrated in an example user interface 350. As with the affordability metrics presented in the GUI presentation 300 of FIG. 3A, the affordability metrics of percentage of employees of the selected client in each affordability band (low, medium, high), this time according to gender (male or female), are presented in bar graph form. As illustrated, for each affordability band 352 (high 352a, medium 352b, and low 352c), comparison bar graphs illustrated percentages of employee broken down by income band 354 (above $100 k 354a, $70 k-100 k 354b, $50-75 k 354c, $30-50 k 354d, and $0-30 k 354e) and further by gender 356 (male 356a, female 356b).

Arranged beneath the bar graphs of the user interface 350, benchmark comparisons are presented demonstrating percentages of employees 358 ("your population") within each affordability band 352 in view of overall (e.g., regional or national) health vulnerability index (HVI) 360 and industry standard HVI 362. Again, each category is broken down by male 356a versus female 356b.

Returning to FIG. 3A, beyond the break-down presentation 308 of affordability metrics, in some embodiments, other GUI presentations may include subscriber population metrics related to chronic conditions 320 (e.g., chronic conditions 164, as analyzed by the chronic condition estimation engine 128 of FIG. 1), subscriber population metrics related to plan utilization 322 (e.g., as analyzed by the participant use analysis engine 118 of FIG. 1), subscriber population metrics related to behavioral risk factors 324 (e.g., as analyzed by the risk factor estimation engine 130 of FIG. 1), and/or subscriber population metrics related to productivity 326 (e.g., as analyzed by the participant attendance impact modeling engine 142 of FIG. 1).

Turning to FIG. 7A, an example GUI presentation 700 portrays a graphical estimate of behavioral risk factors 702 across ADI risk categories 704 (e.g., low ADI risk 704a, medium ADI risk 704b, and high ADI risk 704c). The GUI presentation 700, for example, may be generated based on data supplied by the risk factor estimation engine of FIG. 1. The behavioral risk factors 702 shown include an alcohol consumption risk factor 702a, an obesity risk factor 702b, a tobacco consumption risk factor 702c, and a poor nutrition risk factor 702d. Each of the behavioral risk factors are presented in a bar graph as a number of employees per thousand likely to exhibit the behavior. For example, according to the first risk behavior factor 702a, almost double the number of low ADI risk employees (235/1000) are likely to exhibit alcohol consumption risk than a number of high ADI risk employees (122/1000) regularly consuming alcohol. Conversely, in the third risk factor 702c, high ADI risk employees are over twice as likely (170/1000) than low ADI risk employees (82/1000) to consume tobacco on a regular basis. An employer may review the information, for example, to recognize potential areas for programs (e.g., a gym program to reduce obesity or community supported agriculture program to improve nutrition) for the employee population.

FIG. 7B is an example GUI presentation 710 portraying graphical estimates of medical service utilization 712 across PCP shortage categories 714 (e.g., low PCP shortage 714a, medium PCP shortage 714b, and high PCP shortage 714c) of a population. The GUI presentation 710, for example, may be generated based on data supplied by the participant use analysis engine 118 of FIG. 1. The medical services featured include emergency room visit utilization 712a, preventative visit utilization 712b, generic prescription utilization 712c, behavioral health visit utilization 712d, inpatient visit utilization 712e, and outpatient surgery utilization 712f. Each of the medical service utilization metrics is represented in bar graph form as the number of employees per thousand likely to utilize the particular medical service. An employer reviewing the information contained in the graphical estimates of service utilization 712, for example, can recognize the substantial decline of preventive visits 712b and behavioral health visits 712d where PCP shortages are medium 714b and high 714c, while emergency room visits for areas of high PCP shortages 714c are far greater than in other PCP shortage regions 714a, 714b.

Turning to FIG. 4, an example GUI presentation 400 presents an overview of a subject entity, its employee base, and general health and wellness metrics related to the employee base. As illustrated, the example GUI presentation 400 includes an "about your company" section 402 identifying an industry 406 (e.g., agriculture, forestry, fishing), a number of employees in the health insurance subscriber population 408 (e.g., "employees enrolled" 40,592), a distribution of employees across gender 410 (e.g., 44% female, 56% male), and an average employee age 412 (e.g., 44). Further, the section 402 includes salary information including an average salary 414 (e.g., $91,242) and a salary breakdown table 416 representing both an employee count and a percentage of employees for each displayed salary band (e.g., $0-$30K, $30-$50K, $50-$70K, $70-$100K, and above $100K). Correspondingly, as illustrated in FIG. 3A, when an affordability by income display option 328 is selected, the affordability metrics overview 306 may be replaced with metrics providing details of affordability corresponding to each of the salary ranges. The salary bands, for example, may align with the salary categorizations of the census divisions 172 of FIG. 1. As indicated in a footnote, "salary is estimated for the enrolled household." For example, spouse salaries may be imputed as described, for example, in relation to the method 200 of FIG. 2A.

In an "about your employees" section 404, descriptions of general healthcare metrics are presented, including an affordability metric description 418, an area deprivation index (ADI) description 420, a primary care physician shortage description 422, and a mental health provider shortage description 424. The ADI description 420 may correspond to metrics presented in an example GUI presentation 500 of FIG. 5A (e.g., generated by the social determinants impact analysis engine 146 of FIG. 1). Similarly, the primary care physician shortage description 422 may correspond to metrics presented in an example GUI presentation 520 of FIG. 5B, and the mental health provider shortage description 424 may correspond to an example GUI presentation 540 of FIG. 5C (e.g., generated by the provider shortage impact analysis engine 144 of FIG. 1).

FIG. 5A through FIG. 5C, FIG. 8A, and FIG. 8B illustrate example GUI presentations for reviewing geographic healthcare impacting factor data. The GUI presentations, for example, may be generated by the graphical user interface engine 138 of the health and wellness coverage assessment system 102 of FIG. 1. The metrics presented in the example GUI presentations, for example, may be derived in part from data collected from the health resources 106 and analyzed by the provider shortage impact analysis engine 144 and/or the social determinants impact analysis engine 146.

Turning to FIG. 5A, the example GUI presentation 500 includes a social determinants of health (SDoH) risk analysis overview graph 502, a heat map 504 of ADI measures (e.g., low, medium, and high risk) across the United States, and benchmark comparison metrics 506. The data and metrics used to generate the example GUI presentation 500, for example, may have been determined by the social determinants impact analysis engine 146 of FIG. 1 (e.g., using data collected from one or more of the health resources 106). The example GUI presentation 500, for example, may have been generated by the graphical user interface engine 138 of FIG. 1. The SDoH risk analysis overview graph 502 illustrates a breakdown of employee residence regions (e.g., zip code areas, zip code plus 5 areas, town/city/metropolis, etc.) by ADI risk score. As illustrated, for the subject employer, 29.5% of employees reside in a low ADI risk area, 45.6% live in a medium ADI risk area, and 24.9% live in a high ADI risk area. The benchmark comparison metrics 506 include an overall benchmark SDoH metric set 506a (low SDI risk 30.8%, medium SDI risk 46.1%, and high SDI risk 23.0%) and an industry SDoH metric set 506b (low SDI risk 17.3%, medium SDI risk 43.4%, and high SDI risk 39.3%). The benchmark SDoH metric sets 506, for example, may have been generated by the peer benchmark analysis engine 136 of FIG. 1. The overall benchmark, for example, may take into account all of the entities 104 analyzed by the health and wellness coverage assessment system 102, while the industry benchmark may include each entity 104 matching the industry of the subject client.

Turning to FIG. 5B, the example GUI presentation 520 includes an access to primary care physician (PCP) risk analysis overview graph 522, a heat map 524 of PCP shortage measures (e.g., low, medium, and high shortage) across the United States, and benchmark comparison metrics 526. The data and metrics used to generate the example GUI presentation 520, for example, may have been determined by the provider shortage impact analysis engine 144 of FIG. 1 (e.g., using data collected from one or more of the health resources 106). The example GUI presentation 520, for example, may have been generated by the graphical user interface engine 138 of FIG. 1. The access to PCP risk analysis overview graph 522 illustrates a breakdown of employee residence regions (e.g., zip code areas, zip code plus 5 areas, town/city/metropolis, etc.) by PCP shortage. As noted below the heat map 524, "PCP Shortage is stratified into three groups: High PCP shortage defined as whole county is shortage area; medium PCP shortage defined as part of the county is shortage area; low PCP shortage defined as none of the county is shortage area." As illustrated in the graph 522, for the subject employer, 9.1% of employees reside in a low PCP shortage area, 67.7% live in a medium PCP shortage area, and 23.2% live in a high PCP shortage area. The benchmark comparison metrics 526 include an overall benchmark PCP shortage risk metric set 526a (low PCP shortage risk 7.1%, medium PCP shortage risk 67.4%, and high PCP shortage risk 25.5%) and an industry PCP shortage risk metric set 526b (low PCP shortage risk 6.7%, medium PCP shortage risk 59.1%, and high PCP shortage risk 34.1%). The benchmark PCP shortage risk metric sets 526, for example, may have been generated by the peer benchmark analysis engine 136 of FIG. 1. The overall benchmark metrics 526a, for example, may take into account all of the entities 104 analyzed by the health and wellness coverage assessment system 102, while the industry benchmark metrics 526b may include each entity 104 matching the industry of the subject client.

Turning to FIG. 5C, the example GUI presentation 540 includes an access to mental health providers risk analysis overview graph 542, a heat map 544 of mental health provider shortage measures (e.g., low, medium, and high shortage) across the United States, and benchmark comparison metrics 546. The data and metrics used to generate the example GUI presentation 540, for example, may have been determined by the provider shortage impact analysis engine 144 of FIG. 1 (e.g., using data collected from one or more of the health resources 106). The example GUI presentation 540, for example, may have been generated by the graphical user interface engine 138 of FIG. 1. The access to mental health provider risk analysis overview graph 542 illustrates a breakdown of employee residence regions (e.g., zip code areas, zip code plus 5 areas, town/city/metropolis, etc.) by mental health provider shortage. As noted below the heat map 544, "Mental Health Provider Shortage is stratified into three groups: High shortage defined as whole county is shortage area; medium shortage defined as part of the county is shortage area; low shortage defined as none of the county is shortage area." As illustrated in the graph 542, for the subject employer, 12.9% of employees reside in a low mental health provider shortage area, 24.6% live in a medium mental health provider shortage area, and 62.5% live in a high mental health provider shortage area. The benchmark comparison metrics 546 include an overall benchmark mental health provider shortage risk metric set 546a (low mental health provider shortage risk 16.0%, medium mental health provider shortage risk 36.6%, and high mental health provider shortage risk 47.4%) and an industry mental health provider shortage risk metric set 546b (low mental health provider shortage risk 9.8%, medium mental health provider shortage risk 26.3%, and high mental health provider shortage risk 63.9%). The benchmark mental health provider shortage risk metric sets 546, for example, may have been generated by the peer benchmark analysis engine 136 of FIG. 1. The overall benchmark 546a, for example, may take into account all of the entities 104 analyzed by the health and wellness coverage assessment system 102, while the industry benchmark 546b may include each entity 104 matching the industry of the subject client.

Turning to FIG. 8A, an example GUI presentation 800 includes an average provider cost and quality performance risk analysis overview graph 802, a heat map 804 of provider performance measures (e.g., high performance 808a, medium performance 808b, and low performance 808c) across the United States, and benchmark comparison metrics 806. The data and metrics used to generate the example GUI presentation 800, for example, may have been determined by the affordability analysis engine 126 of FIG. 1 (e.g., using data collected from one or more of the health resources 106) and/or the provider shortage impact analysis engine 144. The example GUI presentation 800, for example, may have been generated by the graphical user interface engine 138 of FIG. 1. The cost & quality performance risk analysis overview graph 802 illustrates a breakdown of percentage of employees residing in areas rated with each average provider performance score 808. As illustrated, for the subject employer, 4.4% of employees reside in one or more regions associated with high provider performance 808a, 87.5% of employees reside in one or more regions associated with medium provider performance 808b, and 8.0% of employees reside in one or more regions associated with low provider performance 808c. The benchmark comparison metrics 806 include an overall HVI 810 and an industry average HVI 812. The benchmark HVI metrics 810, 812, for example, may have been generated by the peer benchmark analysis engine 136 of FIG. 1. The overall benchmark, for example, may take into account all of the entities 104 analyzed by the health and wellness coverage assessment system 102 or all data obtained from the one or more ratings organizations, while the industry benchmark may include each entity 104 matching the industry of the subject client.

FIG. 8B illustrates an example GUI presentation 820, including an access to inpatient providers risk analysis overview graph 822, a heat map 824 of inpatient provider concentration 828 (e.g., low concentration 828a, medium concentration 828b, high concentration 828c, and unknown concentration 828*d*) across the United States, and benchmark comparison metrics 826. The data and metrics used to generate the example GUI presentation 820, for example, may have been determined by the provider shortage impact analysis engine 144 of FIG. 1. The example GUI presentation 820, for example, may have been generated by the graphical user interface engine 138 of FIG. 1. The access to inpatient providers risk analysis overview graph 822 illustrates a breakdown of percentage of employees residing in areas rated with each average inpatient provider concentration measure 828. As illustrated, for the subject employer, 21.0% of employees reside in one or more regions associated with low inpatient provider concentration 828*a*, 18.3% of employees reside in one or more regions associated with medium inpatient provider concentration 828*b*, 40.0% of employees reside in one or more regions associated with high inpatient provider concentration 828*c*, and 20.7% of employees reside in one or more regions for which inpatient provider concentration is unknown 828*d* (e.g., data is not available or is insufficient in metrics). The benchmark comparison metrics 826 include an overall HVI 830 and an industry average HVI 832. The benchmark HVI metrics 830, 832, for example, may have been generated by the peer benchmark analysis engine 136 of FIG. 1. The overall benchmark, for example, may take into account all of the entities 104 analyzed by the health and wellness coverage assessment system 102 or all data obtained from the one or more ratings organizations, while the industry benchmark may include each entity 104 matching the industry of the subject client.

Turning to FIG. 6, an operational flow diagram of a process 600 for simulating affordability across an employee base is illustrated. The process 600, for example, may be performed by a portion of the engines of the health and wellness coverage assessment system 102 of FIG. 1. The process 600, for example, may perform at least portions of the method 200 of FIG. 2A through FIG. 2C on behalf of one of the entities 104 of FIG. 1 for evaluating employee medical benefit affordability.

In some implementations, the process 600 begins with obtaining, at an affordability simulation engine 610, subscriber census data 602 regarding an employee population subscribing to medical insurance coverage offered by an employer, dependents census data 606 regarding dependents (e.g., spouses, children, etc.) of the employees covered by the employer-sponsored medical insurance coverage, and plan design data 604 regarding one or more medical plans offered by the employer to the subscribers. The subscriber census data 602, for example, may include at least portions of the entity population data 112 of FIG. 1, such as the demographics 156, the salary 158, and the coverage tier 162. The plan design data 604, for example, may include the plan design data 160 of FIG. 1. The dependent census data, for example, may include demographics (e.g., age, gender, etc.) of dependents of certain employees (e.g., those having a coverage tier including spouse, child(ren), and/or other dependents).

In some embodiments, if the dependents census data 606 is not provided, the dependents census data 606 is imputed 608 based on the subscriber census data 602. The dependents census data 606 may be imputed, for example, by the dependents modeling engine 120 of FIG. 1.

In some implementations, the affordability simulation engine 610 performs chronic condition modeling 612 according to the subscriber census data 602. The chronic condition modeling may also be performed on at least a portion of the dependents census data 606 (e.g., an adult portion, a portion over a certain age, etc.). The chronic condition modeling, for example, may be performed in a manner similar to that described in relation to the chronic condition estimation engine 128 of FIG. 1. The chronic condition modeling, for example, may generate data similar to the chronic conditions 164 of the census data 114 of FIG. 1.

In some implementations, the modeled chronic conditions are provided for performing behavioral risk factor modeling 614. The behavioral risk factor modeling, for example, may be performed in a manner similar to that described in relation to the behavioral risk factor estimation engine 130 of FIG. 1. The metrics generated by the behavioral risk factor modeling, for example, may be used to produce the graphs of FIG. 7A and FIG. 7B. In other implementations, the behavioral risk factor modeling 614 is performed without input from the chronic condition modeling.

In some implementations, metrics generated by the chronic condition modeling 612 and/or the behavioral risk factor modeling 614 are applied for performing coverage utilization modeling 616. The coverage utilization modeling 616, for example, may be performed in a similar manner as described in relation to the participant use analysis engine 118 of FIG. 1. The coverage utilization modeling 616, for example, may be performed for each insured individual (e.g., employees plus dependents).

In some implementations, for an employee segment of the insured individuals (618), the affordability simulation engine 610 performs time away from work modeling 620 based on the outcome of the coverage utilization modeling 616. The time away from work modeling 620, for example, may be performed in a similar manner as described in relation to the participant attendance impact modeling engine 142 of FIG. 1, for example. The output of the time away from work modeling 620, for example, may be used to generate productivity metrics displayed, for example, in the productivity tab 326 of the user interface of FIG. 3A.

In some implementations, metrics generated through the time away from work modeling 620, in the event of hourly employees (622) as opposed to salaried employees, may be used to adjust the subscriber's anticipated income 624 based on loss of time at work due to medical concerns. This adjustment, for example, can be used as a negative impact to affordability. Further, the adjustment may be applied to calculating the salary band estimates presented in the table 416 of FIG. 4.

In some implementations, the output of the coverage utilization modeling 616 is provided for performing unit cost of utilization modeling 626. The unit cost of utilization modeling 626, for example, may be performed in a similar manner to that described in relation to the affordability modeling engine 124 of FIG. 1. The plan design data 604, for example, may be applied to determining unit costs for service coverage, pharmaceutical coverage, and other covered items (e.g., medical supplies, etc.).

In some implementations, based on the unit cost of utilization modeling 626, an estimated out-of-pocket cost calculation 628 is performed. The estimated out-of-pocket cost calculation 628, for example, may be performed by summing costs accrued by the individual based on the cost of utilization modeling 626.

In some implementations, for subscribers having one or more dependents (630), out-of-pocket costs are aggregated for all plan participants 632 covered under the employee subscriber. The affordability modeling engine 124 of FIG. 1, for example, may aggregate OOP costs across a subscriber household.

In some implementations, the affordability simulation engine 610 performs an estimated total spend calculation 634. The estimated total spend calculation, for example, may combine OOP costs with the employee contribution to plan coverage (e.g., as derived from the plan design data 604). The total spend, for example, may be used to generate the graph 318*a* of FIG. 3A and to calculate the metrics used in the graphs 318*b*-318*d* of FIG. 3A.

In some implementations, the affordability simulation engine 610 determines if the out-of-pocket cost calculation exceeds the out-of-pocket maximum (636). The output of this calculation, for example, may be used to generate the graph 318*e* of FIG. 3A. If the out-of-pocket maximum is exceeded (636), in some embodiments, the affordability simulation engine 610 adjusts the estimated total spend 638.

In some implementations, the estimated total spend and/or the adjusted total spend is used to perform an affordability calculation 640. The affordability simulation engine 610, for example, may apply subscriber income (e.g., derived from the subscriber census data 602 and/or the adjusted total spend 638 to determining affordability across census divisions of the employee population. The affordability calculation 640, for example, may be performed in a similar manner as described in relation to the affordability analysis engine 126 of FIG. 1. The output of the affordability calculation 640, for example, may be used to generate the affordability metrics of the graph 306 and/or the heat map 304 of FIG. 3A. In another example, the output of the affordability calculation 640 may be used to generate the affordability metrics by gender presented in the user interface 350 of FIG. 3C.

Although described in relation to individual modeling and/or calculations on a per subscriber basis, the affordability simulation engine 610 may simulate based on demographic division (e.g., based on the divisions generated by the census generation engine 116 of FIG. 1).

Reference has been made to illustrations representing methods and systems according to implementations of this disclosure. Aspects thereof may be implemented by computer program instructions. These computer program instructions may be provided to a processor of a general-purpose computer, special purpose computer, or other programmable data processing apparatus and/or distributed processing systems having processing circuitry, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors. The virtual processors, for example, may be part of one or more physical computing systems such as a computer farm or a cloud drive.

Aspects of the present disclosure may be implemented by software logic, including machine readable instructions or commands for execution via processing circuitry. The software logic may also be referred to, in some examples, as machine readable code, software code, or programming instructions. The software logic, in certain embodiments, may be coded in runtime-executable commands and/or compiled as a machine-executable program or file. The software logic may be programmed in and/or compiled into a variety of coding languages or formats.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations (e.g., for different object schema dimensions). The hardware logic may be synthesized on a reprogrammable computing chip such as a field programmable gate array (FPGA) or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above.

The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device communicates, such as a server or computer. The processing circuitry and stored instructions may enable the computing device to perform, in some examples, the method 200 of FIG. 2A through FIG. 2C and/or the process 600 of FIG. 6.

These computer program instructions can direct a computing device or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include Wi-Fi®, Bluetooth®, Zigbee®, or another wireless form of communication. The network, for example, may support communications between the health and wellness coverage assessment system 102 and the entities 104, the health resources 106, and/or the providers 108.

The computing device, in some embodiments, further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display. The display controller and display may enable presentation of the screen shots illustrated, in some examples, in FIG. 3A, FIG. 3B, FIG. 3C, FIG. 4, FIG. 5A through FIG. 5C, FIG. 7A, FIG. 7B, FIG. 8A, and/or FIG. 8B.

Moreover, the present disclosure is not limited to the specific circuit elements described herein, nor is the present disclosure limited to the specific sizing and classification of these elements. For example, the skilled artisan will appreciate that the circuitry described herein may be adapted based on changes in battery sizing and chemistry or based on the requirements of the intended back-up load to be powered.

The functions and features described herein may also be executed by various distributed components of a system. For example, one or more processors may execute these system functions, where the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system, in some examples, may be received via direct user input and/or received remotely either in real-time or as a batch process.

Although provided for context, in other implementations, methods and logic flows described herein may be performed on modules or hardware not identical to those described. Accordingly, other implementations are within the scope that may be claimed.

In some implementations, a cloud computing environment, such as Google Cloud Platform™ or Amazon™ Web Services (AWS™), may be used to perform at least portions of methods or algorithms detailed above. The processes associated with the methods described herein can be executed on a computation processor of a data center. The data center, for example, can also include an application processor that can be used as the interface with the systems described herein to receive data and output corresponding information. The cloud computing environment may also include one or more databases or other data storage, such as cloud storage and a query database. In some implementations, the cloud storage database, such as the Google™ Cloud Storage or Amazon™ Elastic File System (EFS™), may store processed and unprocessed data supplied by systems described herein. For example, the contents of the entity data 110, the entity population data 112, the census data 114, and/or the data store 170 of FIG. 1, and/or the subscriber census data 602, the dependents census data 606, and/or the plan design data 604 of FIG. 6 may be maintained in a database structure.

The systems described herein may communicate with the cloud computing environment through a secure gateway. In some implementations, the secure gateway includes a database querying interface, such as the Google BigQuery™ platform or Amazon RDS™. The data querying interface, for example, may support access by the health and wellness coverage assessment system 102 of FIG. 1 to the entity data 110, the entity population data 112, the census data 114, health resources data via the health resources systems 106, provider data via the provider systems 108, and/or entity data via the entity systems 104. In another example, the data querying interface, for example, may support access by the affordability simulation engine 610 of FIG. 6 to the subscriber census data 602, the dependents census data 606, and/or the plan design data 604.

In some implementations, an edge server is used to transfer data between one or more computing devices and a cloud computing environment according to various embodiments described herein. The edge server, for example, may be a computing device configured to execute processor intensive operations that are sometimes involved when executing machine learning processes, such as natural language processing operations. An edge server may include, for example, one or more GPUs that are capable of efficiently executing matrix operations as well as substantial cache or other high-speed memory to service the GPUs. An edge server may be a standalone physical device. An edge server may be incorporated into other computing equipment, such as a laptop computer, tablet computer, medical device, or other specialized computing device. Alternatively or additionally, an edge server may be located within a carrying case for such computing equipment. An edge server, in a further example, may be incorporated into the communications and processing capabilities of a mobile unit such as a vehicle or drone, or may otherwise be located within the mobile unit.

In some implementations, the edge server communicates with one or more local devices to the edge server. The edge server, for example, can be used to move a portion of the computing capability traditionally shifted to a cloud computing environment into the local environment so that any computation intensive data processing and/or analytics required by the one or more local devices can run accurately and efficiently. In some embodiments, the edge server is used to support the one or more local devices in the absence of a connection with a remote computing environment. The edge server may be configured to communicate with the one or more local devices directly or via a network. For instance, the edge server can include a private wireless network interface, a public wireless network interface, and/or a wired interface through which the edge server can communicate with the one or more local devices. In some embodiments, certain local devices may be configured to communicate indirectly with the edge server, for example via another local device. Further, the edge server may be configured to communicate with a remote computing (e.g., cloud) environment via one or more public or private wireless network interfaces.

In some implementations, the method 200 of FIG. 2A through FIG. 2C and/or the process 600 of FIG. 6 may be configured to be performed in part by an edge server or a device interoperating with an edge server. The device interoperating with the edge server, for example, may share processing functionality with the edge server via one or more APIs implemented by the processes.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A system for simulating health expense affordability, the system comprising:

one or more chronic condition models trained to estimate numbers of a population having each of a plurality of chronic conditions, each chronic condition model being trained to estimate a chronic condition distribution based at least in part on geography and/or demography, and one or more utilization machine learning models, each utilization machine learning model being trained to estimate usage of one or more medical plan features of a plurality of medical plan features in view of at least one chronic condition of the plurality of chronic conditions; and processing circuitry configured to perform operations comprising obtaining historic claims data representing populations of a plurality of entities and demographic information of the populations of the plurality of entities, determining chronic conditions of the populations of the plurality of entities, using the historic claims data, the demographic information of the populations of the plurality of entities, and the chronic conditions of the populations of the plurality of entities, training the one or more utilization machine learning models to estimate usage of the plurality of medical plan features in view of the plurality of chronic conditions, obtaining census data regarding a population of individuals, the census data comprising, for each individual, an age or an age range, a gender, and a geographic location, using the census data, assigning each individual of the population of individuals to a plurality of census divisions comprising, for each respective demographic category of a plurality of demographic categories, a respective division within the respective demographic category, applying the plurality of census divisions to the one or more chronic condition models to obtain, for each chronic condition of the plurality of chronic conditions, a respective estimated chronic condition distribution among the plurality of census divisions of the population, providing, to the one or more utilization machine learning models, the plurality of census divisions of the population and the respective estimated chronic condition distribution for each chronic condition of the plurality of chronic conditions, wherein the one or more utilization machine learning models are configured to model, for each respective census division of the plurality of census divisions, a respective estimated utilization of the plurality of medical plan features for a subset of the population belonging to the respective census division as a distribution of usage of each respective plan feature of the plurality of medical plan features, determining, for each respective medical plan feature of the plurality of medical plan features, a unit cost of the respective medical plan feature, wherein the unit cost represents an estimated out-of-pocket cost to at least a portion of the population, using the unit costs of the plurality of medical plan features and the distribution of usage of each respective plan feature of the plurality of medical plan features, calculating a plurality of estimated costs comprising, for each respective census division of the plurality of census divisions, a respective estimated cost to the subset of the population belonging to the respective census division, and calculating, based on income levels across the population, at least one set of metrics representing relative affordability in light of the plurality of estimated costs.

2. The system of claim 1, wherein the processing circuitry is further configured to perform operations comprising imputing, for a subscriber segment of the population of individuals, estimated census data for a plurality of dependents comprising one or more dependents of each subscriber of at least a portion of the subscriber segment, wherein the census data comprises the estimated census data.

3. The system of claim 1, wherein the processing circuitry is further configured to perform operations comprising imputing, for each respective individual of at least a portion of a subscriber segment of the population of individuals, an estimated income level of the respective individual, wherein calculating the at least one set of metrics comprises calculated based on the estimated income levels of the portion of the subscriber segment of the population of individuals.

4. The system of claim 1, wherein the processing circuitry is further configured to perform operations comprising modeling, based at least in part on the respective estimated chronic condition distribution for each census division of the plurality of census divisions, an estimated time away from work across the plurality of census divisions for medical reasons.

5. The system of claim 1, wherein modeling the respective estimated utilization of one or more medical plan features of the plurality of medical plan features comprises modeling based at least in part on provider shortage distributions across geographic divisions of the population.

6. The system of claim 1, wherein the processing circuitry is further configured to perform operations comprising calculating, based on geographic distributions across the population, at least one set of social determinants representing relative levels of social determinant of health risk across the population.

7. The system of claim 1, wherein determining the chronic conditions of the populations of the plurality of entities comprises imputing, based on codings of the historic claims data, the chronic conditions.

8. The system of claim 1, wherein the processing circuitry is further configured to perform operations comprising calculating an estimated total spend exceeding a threshold percentage of income.

9. The system of claim 8, wherein the processing circuitry is further configured to perform operations comprising calculating, using a respective medical plan contribution level associated with each individual of the population, a respective estimated total spend per census division of the population and further per the respective medical plan contribution level.

10. The system of claim 1, wherein the processing circuitry is further configured to perform operations comprising modeling, for each respective census division of the plurality of census divisions, a respective estimated risk factor distribution for each risk factor of a set of risk factors.

11. The system of claim 10, wherein the set of risk factors comprises tobacco use, alcohol abuse, obesity, and/or poor nutrition.

12. The system of claim 1, wherein the processing circuitry is further configured to perform operations comprising calculating, based on the respective estimated utilization of one or more medical plan features of the plurality of medical plan features, an estimated utilization rate for each census division of the plurality of census divisions.

13. The system of claim 12, wherein the one or more medical plan features comprises at least one of emergency room visits, preventative care visits, behavioral health visits, inpatient hospital visits, or outpatient surgical visits.

14. A method for modeling health care affordability and health care availability across a population of individuals, the method comprising:

modeling the health care affordability by obtaining, by processing circuitry, historic claims data representing populations of a plurality of entities and demographic information of the populations of the plurality of entities, determining, by the processing circuitry, chronic conditions of the populations of the plurality of entities, using the historic claims data, the demographic information of the populations of the plurality of entities, and the chronic conditions of the populations of the plurality of entities, training one or more utilization machine learning models to estimate usage of a plurality of medical plan features in view of a plurality of chronic conditions, determining, by the processing circuitry, census data regarding the population of individuals, the census data comprising, for each individual, an age or an age range, a gender, and a geographic location, determining, by the processing circuitry, an income level distribution across the population of individuals, using the census data, segmenting, by the processing circuitry, the population of individuals into a plurality of census divisions, the plurality of census divisions comprising, for each respective demographic category of a plurality of demographic categories, a respective division within the respective demographic category, for each chronic condition of the plurality of chronic conditions, determining, by the processing circuitry, a respective estimated chronic condition distribution among the plurality of census divisions, providing, to the one or more utilization machine learning models, the plurality of census divisions of the population of individuals and the respective estimated chronic condition distribution for each chronic condition of the plurality of chronic conditions, wherein the one or more utilization machine learning models are configured to model, for each respective census division of the plurality of census divisions, a respective estimated utilization of the plurality of medical plan features for a subset of the population of individuals belonging to the respective census division as a distribution of usage of each respective plan feature of the plurality of medical plan features, for each respective medical plan feature of the plurality of medical plan features, determining, by the processing circuitry, at least one unit cost of the respective medical plan feature, wherein the unit cost represents an estimated out-of-pocket cost to at least a portion of the population, by the processing circuitry, using the unit costs of the plurality of medical plan features and the distribution of usage of each respective plan feature of the plurality of medical plan features, calculating a plurality of estimated costs comprising, for each respective census division of the plurality of census divisions, at least one respective estimated cost to a portion of the population of individuals belonging to the respective census division, and using the income level distribution, calculating, by the processing circuitry based at least in part on the plurality of estimated costs, at least one set of metrics representing relative affordability;

using the geographic location of the census data for each member of the population of individuals, modeling the health care availability by calculating, by the processing circuitry, at least one distribution of health provider shortages for the population of individuals; and preparing, by the processing circuitry for presentation via a graphical user interface, a presentation comprising the at least one set of metrics and the at least one distribution of health provider shortages.

15. The method of claim 14, wherein modeling the health care availability comprises, using the geographic location of the census data for each member of the population, calculating, by the processing circuitry, at least one distribution of social determinants of health risks for the member population.

16. The method of claim 14, wherein the at least one distribution of health provider shortages comprises a distribution of mental health provider shortages, and a distribution of primary care physician shortages.

17. The method of claim 14, further comprising:

for each individual of the population of individuals, determining, by the processing circuitry, a respective medical plan of a set of possible medical plans;

wherein, for at least a portion of the plurality of medical plan features, determining the at least one unit cost comprises modeling, for each respective medical plan of the set of possible medical plans, an estimated unit cost for subscribers of the respective medical plan.

18. The method of claim 14, further comprising:

for each individual of the population of individuals, determining, by the processing circuitry, a respective medical plan of a set of possible medical plans;

wherein calculating the at least one set of metrics representing relative affordability comprises calculating the at least one set of metrics based further on an employee contribution corresponding to each respective medical plan of the set of possible medical plans.

19. The method of claim 14, wherein the presentation is an interactive web-based presentation.

* * * * *